(12) United States Patent
Shelley et al.

(10) Patent No.: US 7,992,612 B2
(45) Date of Patent: Aug. 9, 2011

(54) RESEARCH PRESS

(75) Inventors: Stuart James Shelley, Cincinnati, OH (US); Richard Allan Roth, II, Blue Ash, OH (US); Allan Michael Burwinkel, Cincinnati, OH (US); Richard William Hamm, Loveland, OH (US); Larry Ray Gilliam, Jr., Sparta, KY (US)

(73) Assignee: The Procter and Gamble Company, Cincinnati, OH (US)

( * ) Notice: Subject to any disclaimer, the term of this patent is extended or adjusted under 35 U.S.C. 154(b) by 664 days.

(21) Appl. No.: 11/937,034

(22) Filed: Nov. 8, 2007

(65) Prior Publication Data
US 2009/0120308 A1 May 14, 2009

(51) Int. Cl.
B32B 41/00 (2006.01)
(52) U.S. Cl. .................. 156/351; 156/358; 156/360
(58) Field of Classification Search .......... 156/351, 156/358, 360; 100/48; 73/763, 866, 866.4
See application file for complete search history.

(56) References Cited

U.S. PATENT DOCUMENTS

| | | |
|---|---|---|
| 3,640,127 A | 2/1972 | Meissner |
| 3,795,134 A | 3/1974 | Eichenbrenner et al. |
| 4,069,702 A | 1/1978 | Hayner |
| 4,074,624 A | 2/1978 | Biornstad et al. |
| 4,420,958 A | 12/1983 | Schulz et al. |
| 4,623,419 A * | 11/1986 | Price ............................ 156/502 |
| 4,691,576 A | 9/1987 | Schleuniger et al. |
| 4,812,722 A | 3/1989 | Corrothers |
| 4,854,984 A | 8/1989 | Ball et al. |
| 4,919,738 A | 4/1990 | Ball et al. |
| 5,167,799 A | 12/1992 | Severin et al. |
| 5,188,456 A | 2/1993 | Burke et al. |
| 5,351,553 A | 10/1994 | Lepie et al. |
| 5,375,315 A * | 12/1994 | Griffith et al. .................. 29/432 |
| 5,386,092 A | 1/1995 | Dufrenne |
| 5,438,863 A | 8/1995 | Johnson |
| 5,515,294 A | 5/1996 | Mohr et al. |
| 5,562,027 A | 10/1996 | Moore |
| 5,575,078 A | 11/1996 | Moulton, III |
| 5,767,402 A | 6/1998 | Sandlass et al. |
| 5,974,853 A | 11/1999 | Strong et al. |
| 6,114,965 A * | 9/2000 | Schoch ........................ 340/680 |
| 6,145,563 A | 11/2000 | Kalisiak et al. |
| 6,248,195 B1 | 6/2001 | Schmitz |
| 6,370,962 B1 * | 4/2002 | Sullivan et al. ................. 73/826 |
| 6,410,820 B1 | 6/2002 | McFall et al. |
| 6,418,828 B1 | 7/2002 | Kalnitz |
| 6,500,377 B1 | 12/2002 | Schneider et al. |

(Continued)

OTHER PUBLICATIONS

PCT International Search Report dated Apr. 20, 2009.

*Primary Examiner* — George R Koch, III
(74) *Attorney, Agent, or Firm* — Megan C. Hymore; James E. Oehlenschlager

(57) ABSTRACT

A simulation press having a main body and an actuator attached thereto. The actuator is substantially aligned with the main body. A first plate is coupled to the main body and a second plate is coupled to the actuator. Both plates are adapted to engage a workpiece so as to simulate various modes of deformation of an area or areas on the workpiece when the second plate is moved relative to the first plate. The simulation press further includes a drive controller for controlling operation of the actuator. The drive controller additionally responds to feedback from at least one feedback sensor included with the simulation press.

19 Claims, 25 Drawing Sheets

U.S. PATENT DOCUMENTS

| | | |
|---|---|---|
| 6,539,809 B1 | 4/2003 | Weiss et al. |
| 6,843,134 B2 | 1/2005 | Anderson et al. |
| 6,915,700 B2 | 7/2005 | Anderson et al. |
| 7,024,939 B2 | 4/2006 | Anderson et al. |
| 7,062,983 B2 * | 6/2006 | Anderson et al. ............ 73/866.4 |
| 2005/0262948 A1 * | 12/2005 | Anderson et al. ............... 73/763 |

* cited by examiner

RESEARCH PRESS

FIELD OF THE INVENTION

The present invention relates to an apparatus and method for simulating a production line process, and more particularly to an apparatus and method for simulating various modes of deformation of an area or areas on a workpiece in a nip type process. The present invention also relates to an apparatus and method for a variety of fundamental material testing applications/modes including, but not limited to, simple compression, planar, simple shear, oscillatory viscoelasticity, etc.

BACKGROUND OF THE INVENTION

A variety of processes are used on production lines. Examples, include compression loading, such as fusion bonding processes, which may be performed on a plurality of point sites of, or discrete locations on, a workpiece/web material in a nip type process. See, for example, U.S. Pat. Nos. 4,854,984 and 4,919,738. A fusion bonding process, for example, may involve passing a workpiece, such as a thermoplastic dual-layer web material, through a nip defined by two rolls, wherein one roll is provided with a plurality of protuberances. By compressing the workpiece/web material at point sites between the rolls via the protuberances, friction bonds may be effected at those sites. That is, the material at each point site is caused to flow or melt. If the workpiece/web material comprises two or more layers, those layers may be caused to bond to one another at each site. In a production-type process, however, the precise load and gap that the workpiece/web material experiences typically cannot be accurately measured for several reasons, including but not limited to accuracy limits on pressure gauges, the inclusion of equipment inertial loads, vibrations of the equipment and the effect of those vibrations on the gap at the nip point, etc.

It would be desirable to have a press that can simulate processes at speeds that are in-line with current and actual production process speeds. It also would be desirable to have a press that can accurately measure what a workpiece or web material experiences during various production processes.

BRIEF SUMMARY OF THE INVENTION

The present invention, in one embodiment, is a simulation press comprising a main body having an actuator attached thereto such that the actuator is substantially axially aligned with a longitudinal axis of symmetry of the main body. The actuator has a moving face which moves generally in a straight line along the longitudinal axis of symmetry of the main body in the same plane as the main body. A first plate is operably coupled to the main body. The first plate is adapted to engage a workpiece. A second plate is operably coupled to the actuator for movement with a moving face of the actuator. The second plate is adapted to engage the workpiece. The press also includes a drive controller coupled to the actuator for controlling the operation of the actuator in response to feedback from at least one feedback sensor so as to cause the second plate to move relative to the first plate such that the first and second plates engage at least one point site on the workpiece.

The present invention, in another embodiment, is a method of simulating loading of an area on a workpiece in a production line type process including the steps of providing a workpiece comprising at least one layer; providing a first plate having a first surface, the first plate being operably coupled to a base; providing a second plate having a second surface, the second plate being operably coupled to an armature of an actuator, the actuator being further coupled to the base such that the direction of movement of the armature of the actuator is substantially axially aligned with a longitudinal axis of symmetry of the base and generally lies in the same plane as the base; and moving one of the first and second plates relative to the other of the first and second plates such that the first and second surfaces compress a point site on the workpiece so as to simulate compression loading of a point site on a workpiece in a production line type process.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the present invention, it is believed that the invention will be better understood from the following description taken in conjunction with the accompanying Figures, in which:

DETAILED DESCRIPTION OF THE INVENTION

Figure 1:
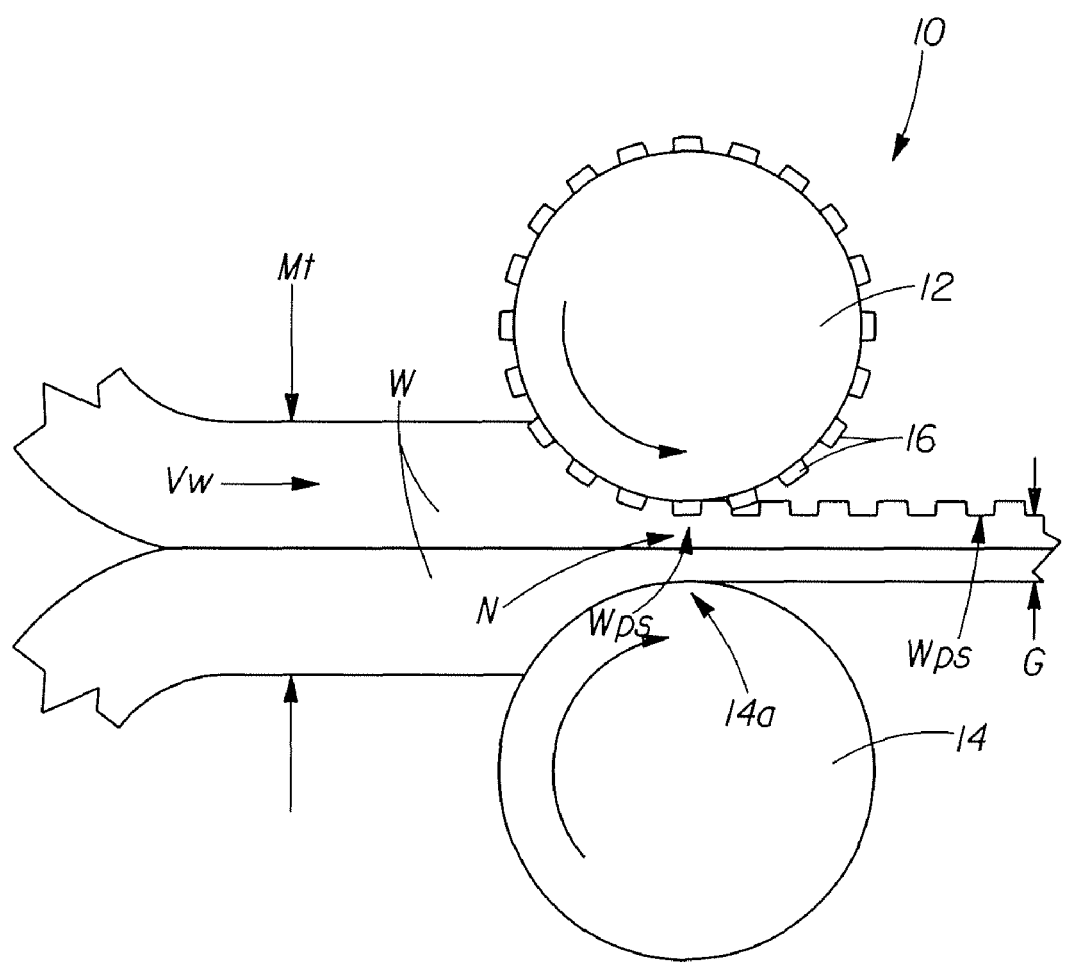
FIG. 1 is a schematic view of first and second rolls effecting a nip type process.

The present invention is a novel and advantageous press for simulating manipulation of a workpiece or web material during a production line process or during various other deformation processes or testing of the workpiece's mechanical response. Any of a variety of production line processes can be simulated with the invention described herein, including but not limited to compression loading on a point site of a workpiece/web material. Simulated compression loading can include, but is not limited to, that effected by fusion bonding rolls. As shown in FIG. 1, a fusion bonding process and system 10 may involve passing a workpiece W, such as a thermoplastic dual-layer web material, through a nip N defined by rolls 12 and 14, wherein the first roll 12 may be provided with a plurality of protuberances 16. By compressing the workpiece/web material at point sites $W_{PS}$ via the protuberances 16, friction bonds may be effected at those sites. That is, the material at each point site $W_{PS}$ may be caused to flow or melt. If the workpiece/web material comprises two or more layers, those layers can be caused to bond to one another at each site. In some embodiments, it may not be desirable to cause the material to flow or melt during the production line process. In certain embodiments, operations other than compressing a point site may be performed on a production line, such as but not limited to stretching, cutting, perforating, etc. In certain embodiments, a production line process may involve any roll speed, force, cut, perforation, bond, etc. Example workpiece materials comprise thermoplastic webs, films, fibrous or particulate agglomerations, composites made of one or more of the preceding materials, etc., such as polyethylene webs, films, etc. These materials may comprise one or more layers of any suitable thickness. For example, each layer can be between about 0.05 mm and about 5 mm, between about 0.1 mm and about 10 mm, less than 0.05 mm, or greater than about 10 mm.

With reference again to FIG. 1, during one type of production line process, such as a nip type process, a protuberance 16 and a corresponding section 14a of an engaging or second roll 14 may compress a point site $W_{PS}$ on a workpiece W a sufficient amount, to a sufficient temperature, and at a sufficient speed, so as to cause the material at the point site $W_{PS}$ to flow or melt due to quasi-adiabatic inelastic heat generation. If the workpiece W comprises two or more layers of material, those layers may be bonded together. It is noted that during a fusion bonding operation, the protuberance 16 and the corresponding section 14a may be at a temperature substantially equal to ambient temperature or heated to a temperature above ambient. In some embodiments, it may not be desirable to cause the material to flow or melt. In certain embodiments, other operations other than compressing a point site may be simulated, such as but not limited to stretching, cutting, perforating, etc. In certain embodiments, any roll speed, force, cut, perforation, bond, etc. may be simulated using the press of the present invention. For example, in some embodiments, it may be desirable to test boundary conditions of a sample workpiece processing method by simulating both ideal and non-ideal, expected and unexpected, calculated and non-calculated, etc. roll speeds, forces, cuts, perforations, bonds, etc. Additionally, in some embodiments, it may be desirable to perform a variety of material testing applications/modes including, but not limited to, simple compression, planar, simple shear, oscillatory viscoelasticity, etc. In certain embodiments, the invention described herein may be used to simulate the shaking that a workpiece may experience during a production line process, such as folding.

Figure 2A:
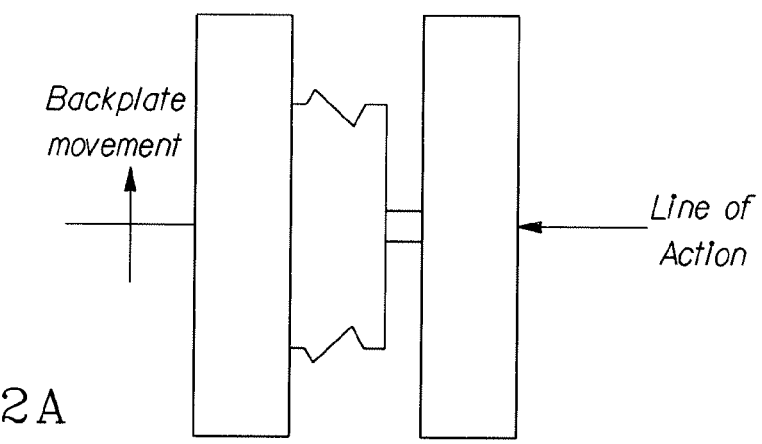
FIG. 2A is a schematic view of multiaxial loading using a press in accordance with an embodiment of the present invention.
Figure 2B:
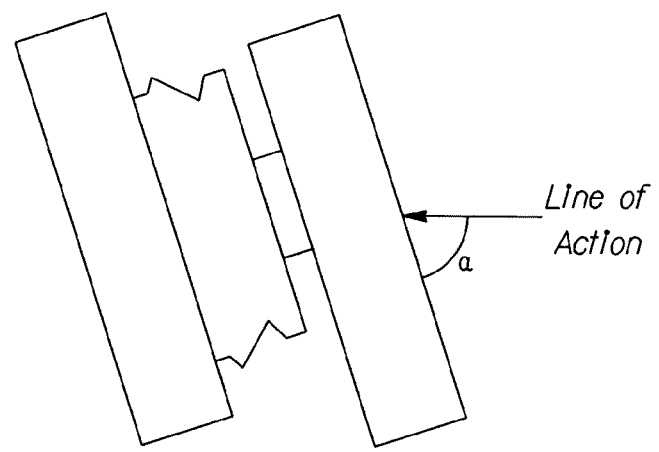
FIG. 2B is a schematic view of multiaxial loading using a press in accordance with an embodiment of the present invention.
Figure 2C:
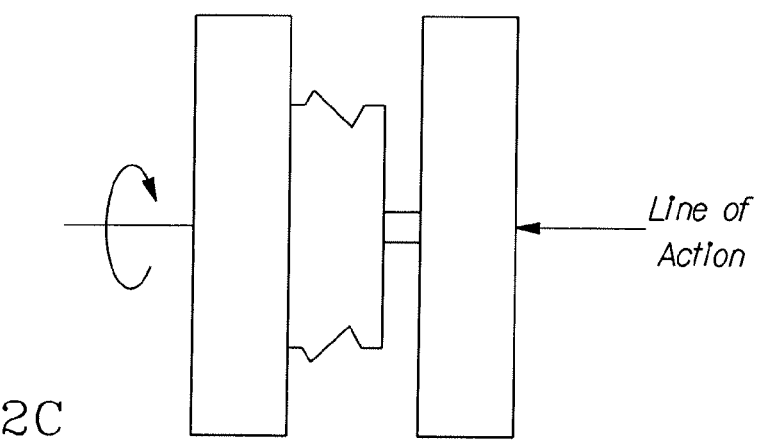
FIG. 2C is a schematic view of multiaxial loading using a press in accordance with an embodiment of the present invention.

In certain embodiments, the invention described herein may be used to simulate combined multiaxial loading. Combined multiaxial loading may be used to understand a material's yield surface hardening behaviors as well as mimic production conditions. In production environments, for example, sometimes one of the roll's, e.g., roll 12 or 14, surface speed is slightly faster than the mating roll. This differential surface speed could be simulated by applying a representative speed during the press event by moving either tooling plate (discussed in detail below) with respect to the other tooling plate, perpendicular to the actuator's line of action, as illustrated in FIG. 2A. In one embodiment, combined loading including compression and transverse shearing through the thickness of the material could be simulated by positioning the tooling plates at an angle α with respect to the actuator's line of action, as illustrated in FIG. 2B. In certain embodiments, combined loading including compression and in-plane shearing could be simulated by rotating either tooling plate with respect to the other tooling plate, as illustrated in FIG. 2C. It is recognized that other combined multiaxial loading simulations may be performed using the various embodiments of the press described herein.

Figure 3A:
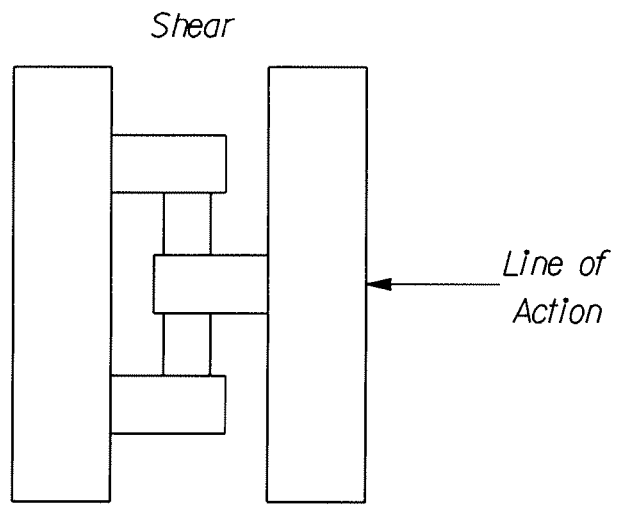
FIG. 3A is a schematic view of a shearing simulation using a press in accordance with an embodiment of the present invention.
Figure 3B:
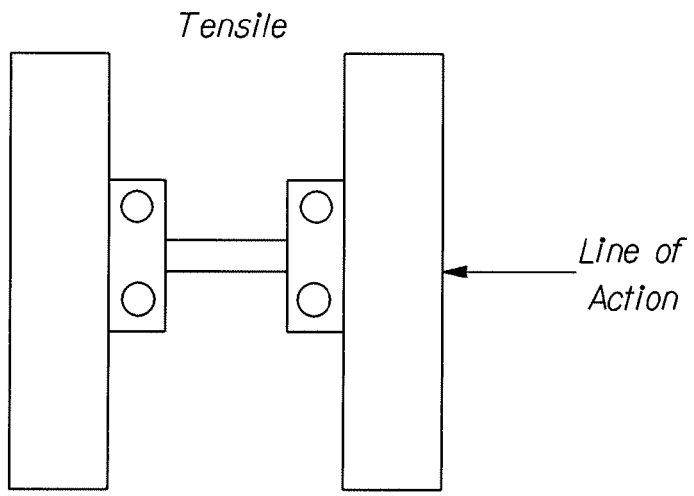
FIG. 3B is a schematic view of tensile loading using a press in accordance with an embodiment of the present invention.
Figure 3C:
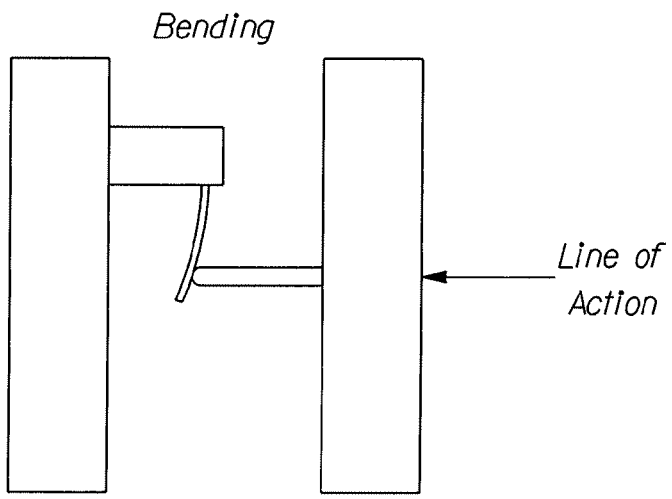
FIG. 3C is a schematic view of a bending simulation using a press in accordance with an embodiment of the present invention.
Figure 4A:
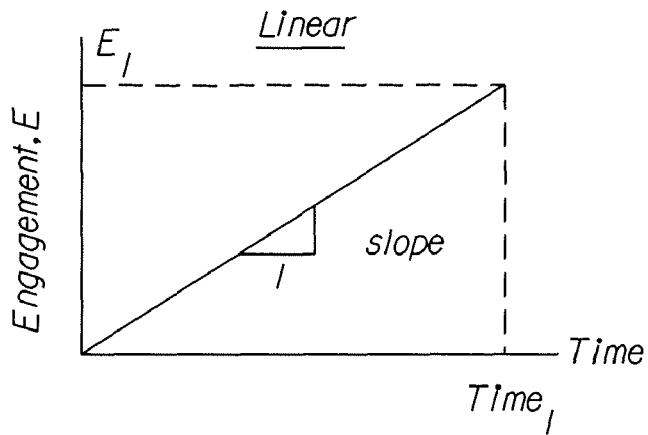
FIG. 4A is a graph of an engagement profile for a press in accordance with an embodiment of the present invention.
Figure 4B:
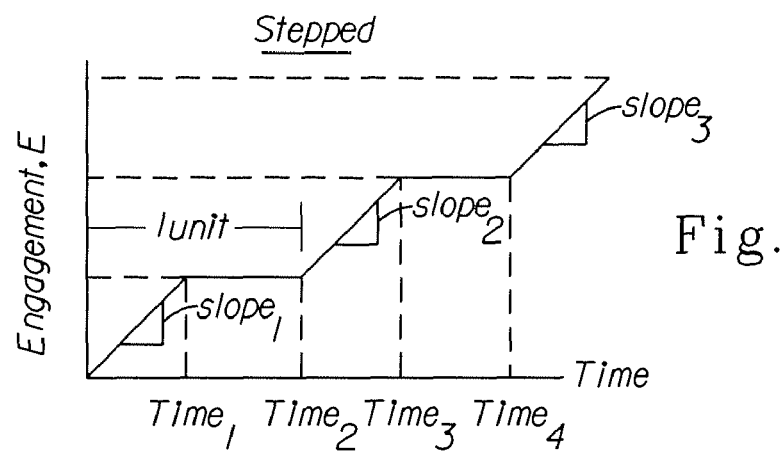
FIG. 4B is a graph of an engagement profile for a press in accordance with an embodiment of the present invention.
Figure 4C:
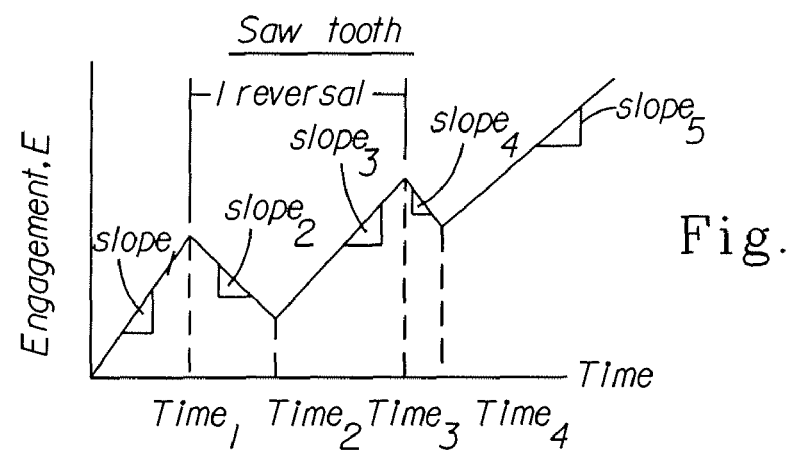
FIG. 4C is a graph of an engagement profile for a press in accordance with an embodiment of the present invention.

In certain embodiments, the present invention may be used to measure and understand a material's mechanical response during various processes, as well as measuring a material's constitutive properties. This may allow links to be made between material properties, process conditions, and product quality and performance. The press of the present invention, for example, may be used to simulate or test shearing, tensile loading, and bending, as illustrated in FIGS. 3A, 3B, and 3C. Example test profiles for example simulations, such as the above example simulations, are illustrated in FIGS. 4A, 4B, and 4C. In one embodiment, tensile loading may be realized on the press via activation. In certain embodiments, as illustrated in FIG. 3B, tensile loading may be implemented by causing the actuator to move away from the backplate assembly (discussed in detail below) rather than toward it. In certain embodiments, lab shear loading may be possible.

Figure 5A:
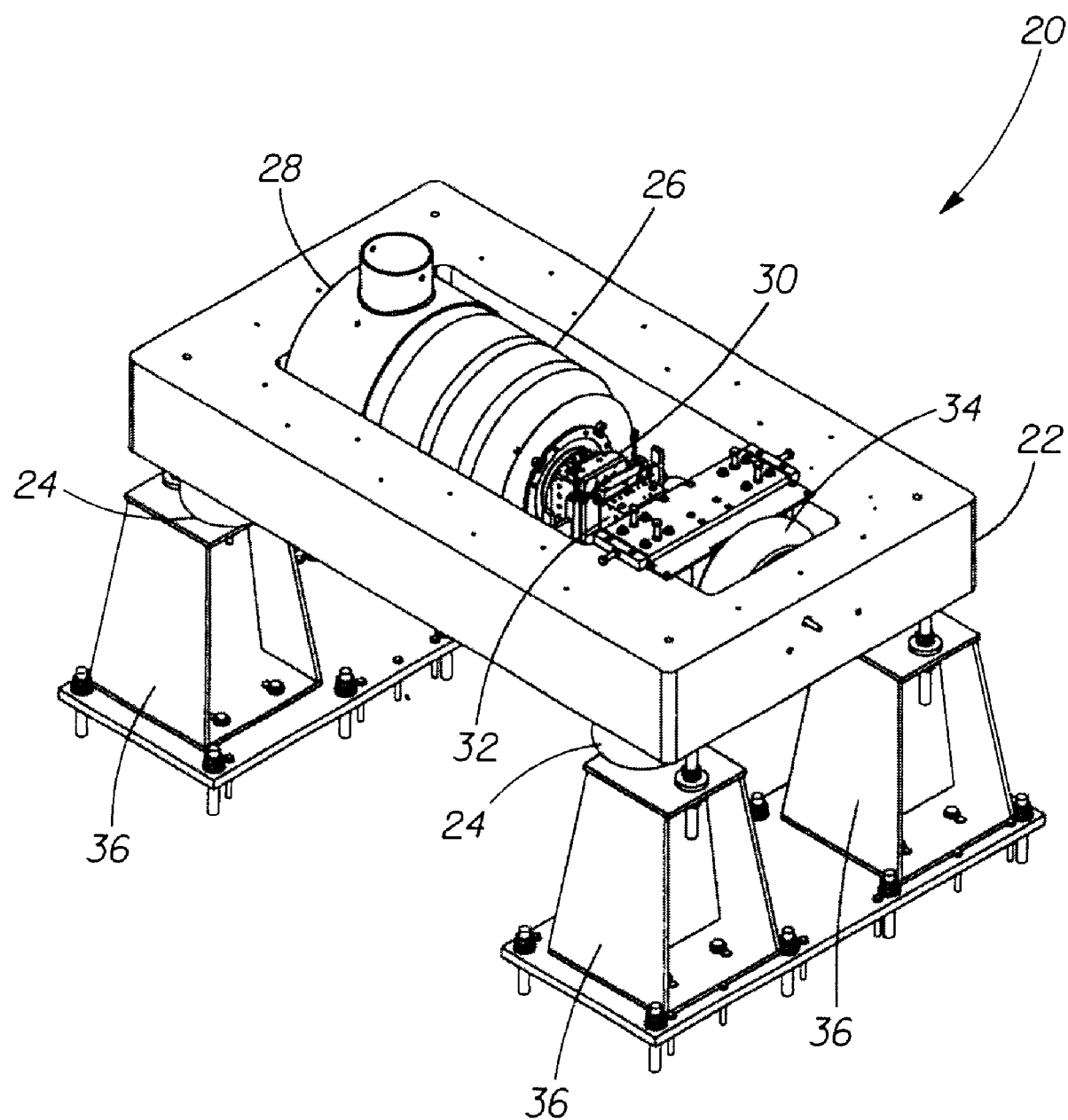
FIG. 5A is a perspective view of a press in accordance with an embodiment of the present invention.
Figure 5B:
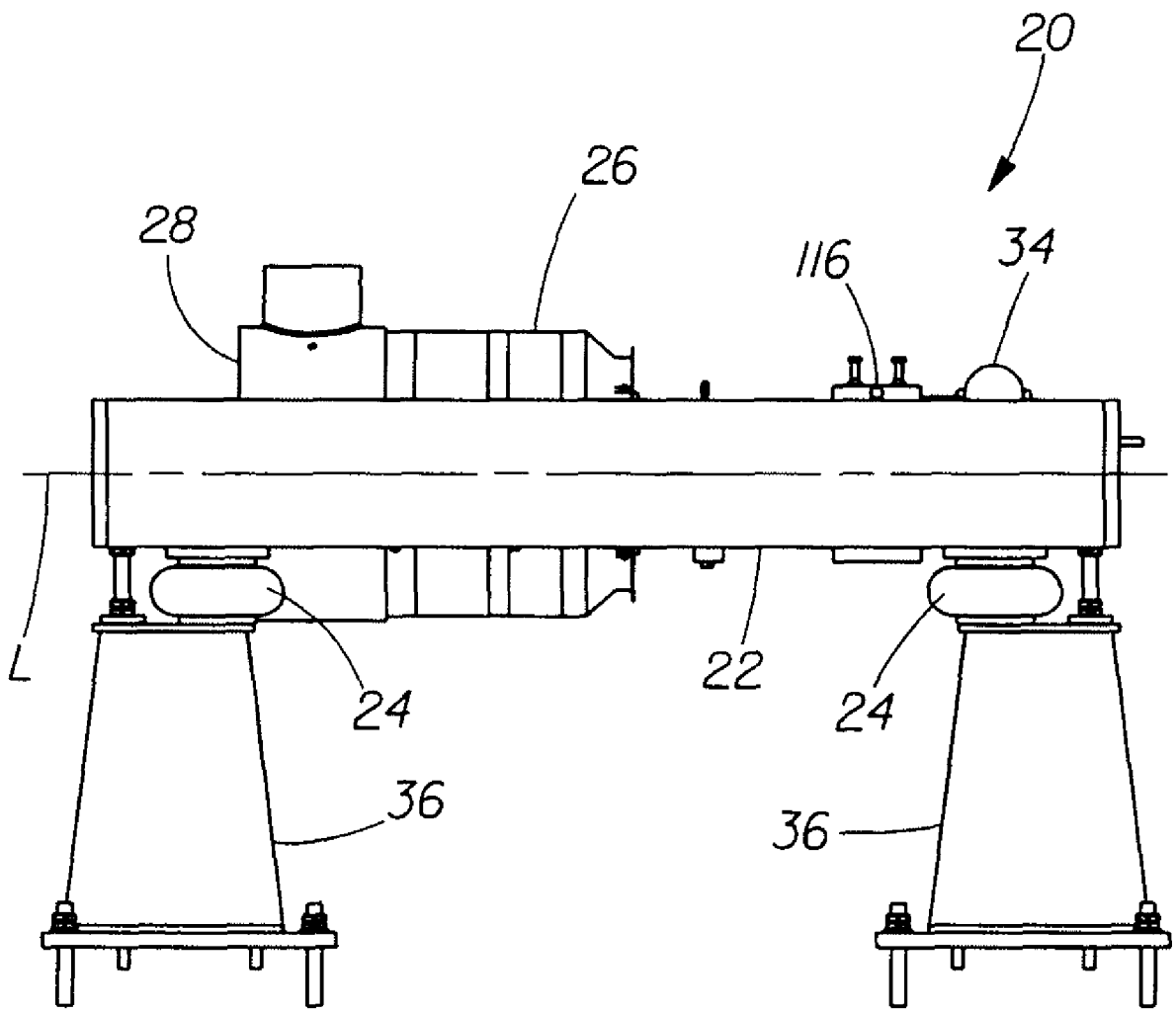
FIG. 5B is a side view of a press in accordance with an embodiment of the present invention.
Figure 5C:
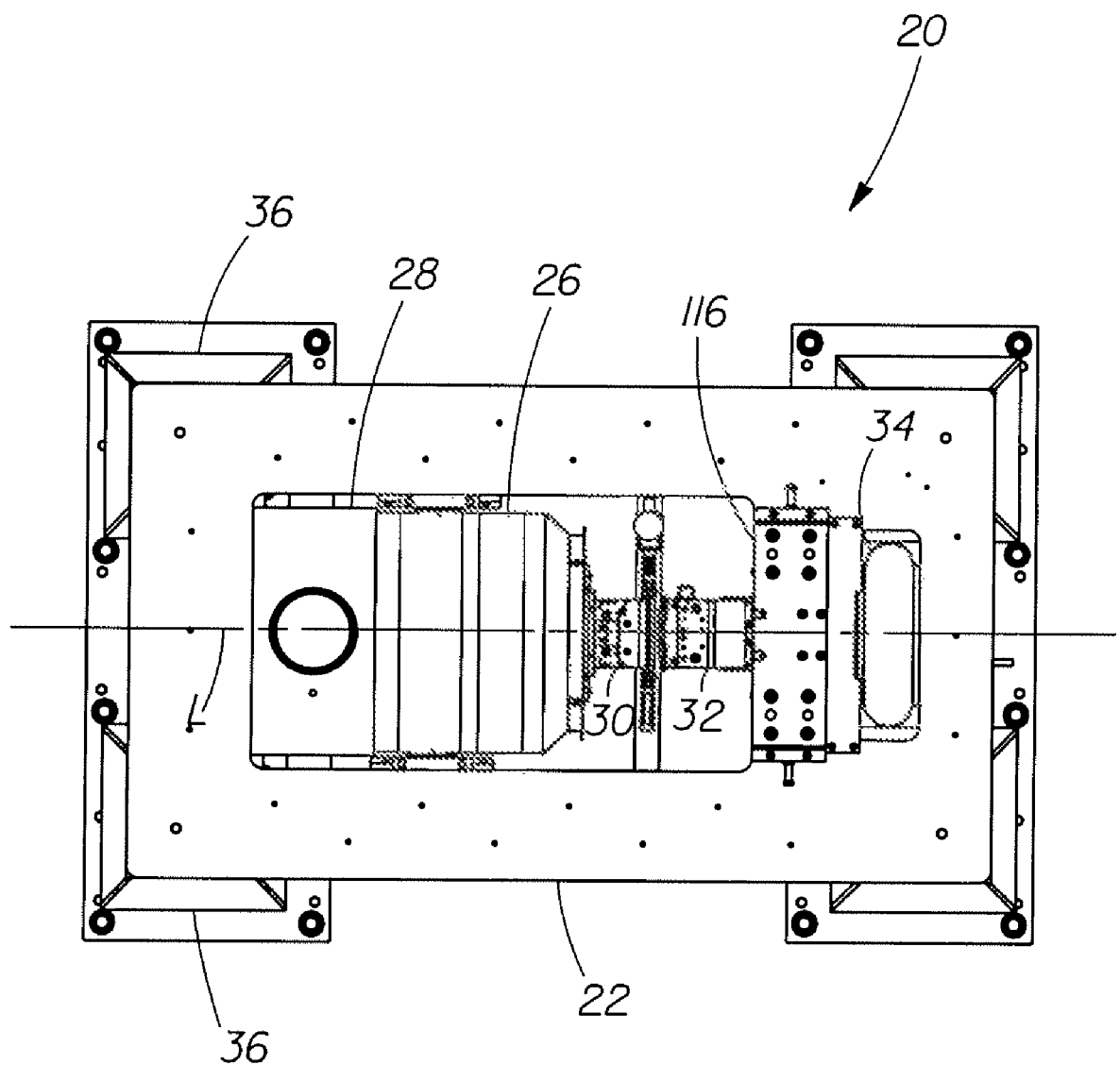
FIG. 5C is a top view of a press in accordance with an embodiment of the present invention.

An embodiment of a press 20 in accordance with the present invention is illustrated in FIGS. 5A through 5C. The press 20 may generally comprise some or all of pedestals 36, a base 22, support air bags 24, actuator 26, back actuator support 28, moving plate assembly 30, backplate assembly 32, and backplate air bag 34. As can be seen from FIGS. 5B and 5C, actuator 26 may be positioned generally axially on a longitudinal axis of symmetry of base 22 (shown as dashed line 'L'). Longitudinal axis L, in some embodiments, may be located generally equidistant from a top and bottom surface of base 22 and generally equidistant from side surfaces of base 22. That is, longitudinal axis L may be located generally along a central, longitudinal axis of symmetry of base 22. In other words, actuator 26 may be positioned generally in the same plane as base 22. This may have the benefit that inertial forces associated with acceleration of the armature of the actuator 26 may then generally not exert bending forces on base 22 and excite out-of-plane vibration modes of base 22.

Figure 6:
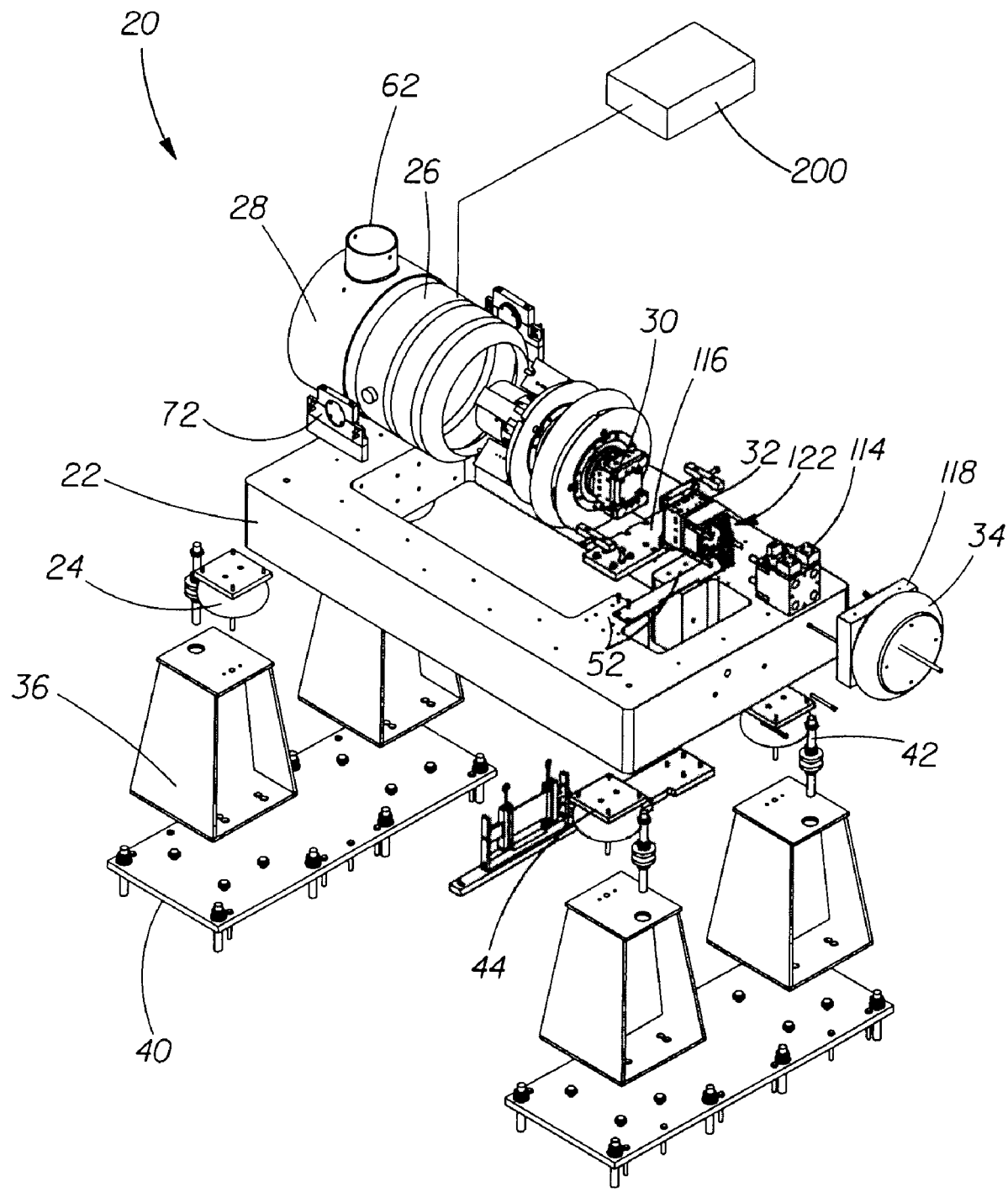
FIG. 6 is an exploded schematic view of a press in accordance with an embodiment of the present invention.

With reference to FIG. 6, an exploded view of a further embodiment of a press 20 in accordance with the present invention is illustrated. The press 20 may generally comprise some or all of sole plates 40, pedestals 36, support air bags 24, top plates 44, safety stops 42, base 22, trunion block support 72, actuator 26, back actuator support 28, exhaust 62, moving plate assembly 30, backplate assembly 32, upper girdle 116, linear bearings 122, inlet areas 52, backblock 114, safety release plate 118, backplate air bag 34, and drive controller 200. It is recognized that the aforementioned elements do not form a list, partial or complete, of required press components, nor do the aforementioned elements form an exhaustive list of all the components that may be used in accordance with the present invention. That is, several of the components shown in FIG. 6 may be removed, or further components may be included, to achieve an embodiment of a press 20 in accordance with the present invention.

With regard to fastening, mounting, attaching, or connecting the components of the press of the present invention to form the system as a whole, unless specifically described otherwise, such are intended to encompass fastening by any suitable method. Examples of suitable fastening methods include the use of conventional fasteners such as screws, nut and bolt connectors, rivets, toggles, pins, and the like. Furthermore, components may also be connected or coupled, where appropriate, by welding, friction fitting, deformation, etc. Electrical components and connections may be made using appropriate electrical components and connection methods, including conventional components and connectors. Measuring devices for measuring load, acceleration, etc., may be selected from such measuring devices that are suitable for use in the present invention. For example, devices such as sensors, transducers, and the like may be selected from any such measuring devices suitable for use in the present invention. Unless otherwise specifically disclosed or taught, materials for making components of the present invention may be selected from any appropriate materials, which include but are not limited to materials such as metal, metallic alloys, fibers, plastics, ceramic, and the like, and any suitable combinations of these. Similarly, any materials for making components of the present invention may be manufactured by any appropriate manufacturing and/or production methods including casting, extruding, molding, and machining.

Figure 7:
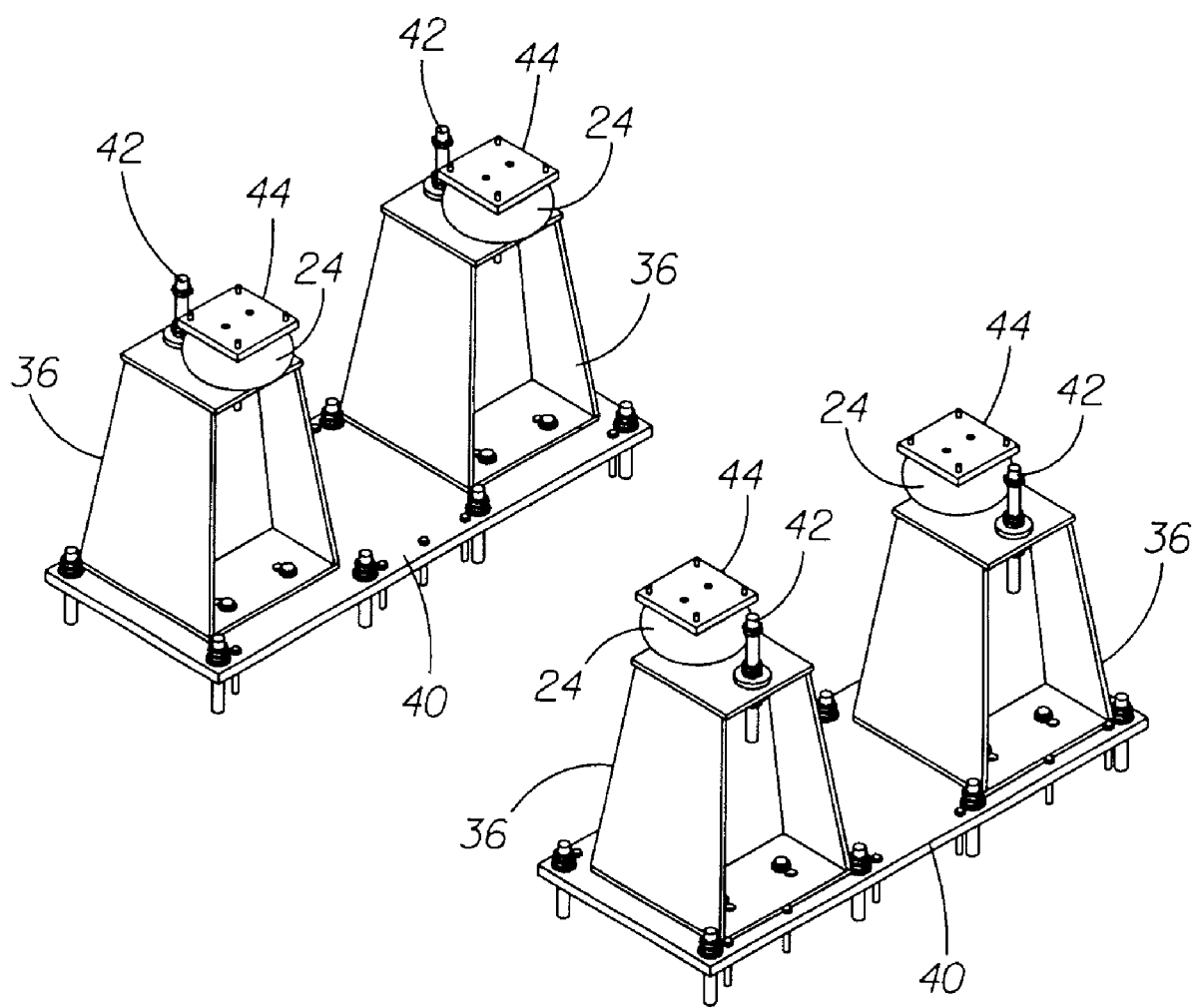
FIG. 7 is perspective view of pedestals of a press in accordance with an embodiment of the present invention.

With reference to FIG. 7, an embodiment of press 20 may include sole plates 40. Sole plates 40 optionally may be securely attached to the ground by any suitable manner, including but not limited to, bolting the sole plates 40 to the ground, welding the sole plates 40 to the ground, etc. Alternatively, sole plates 40 need not be securely attached to the ground. Pedestals 36 may be mounted on top of sole plates 40. Any means of mounting pedestals 36 to the sole plates 40 may be used to mount pedestals 36 to the sole plates 40. In an embodiment shown in FIG. 7, pedestals 36 may be mounted to sole plates 40 with bolts. Although there are four pedestals 36 illustrated in FIG. 7, it is recognized that a fewer or greater number of pedestals 36 may be used, as desired. It is again recognized that all components of press 20 discussed in detail may not be necessary. For example, sole plates 40 may be excluded from some embodiments of press 20. Similarly, pedestals 36 may be excluded from some embodiments of press 20, for example where press 20 may be suspended from a ceiling or other suitable structure.

In some embodiments, support air bags 24 may be provided. Support air bags 24 may be mounted as desired, including on top of pedestals 36, and between pedestals 36 and base 22. In certain embodiments, support air bags 24 may include a top plate 44 for attaching base 22 to support air bags 24. In other embodiments, top plate 44 may be excluded. In certain embodiments of press 20, it may be desirable to isolate the base, and thus isolate the attached parts, including the actuator 26, moving plate assembly 30, and backplate assembly 32. Therefore, support air bags 24, in some embodiments, may help isolate these components from the external environment, e.g., external background vibrations, as the external environment may taint any data obtained by the press 20. That is, support air bags 24 may isolate base 22 and attached parts from, for example, but not limited to, external vibrations and external noise into the system. The support air bags 24 may also isolate the external environment from vibrations caused by the press 20. It is recognized that, in some embodiments, support air bags 24 need not be provided.

Pedestals 36, in an embodiment, may further include safety stops 42. Safety stops 42 may be securely mounted to the tops of pedestals 36, near the support air bags 24, and slidably connect to base 22. In alternate embodiments, safety stops 42 may be securely mounted to base 22 and slidably connect to the tops of the pedestals 36, near the support air bags 24. Safety stops 42 may provide support to base 22 in the event a support air bag 24 fails. In a further embodiment, safety stop 42 may maintain base 22 on a pedestal 36 in the event a support air bag 24 fails. Similarly, safety stops 42 may maintain base 22 on the pedestals 36 during unexpected or accidental incidents, such as an earthquake or any other incident where base 22 could otherwise fall off the pedestals, such as the press 20 being accidentally struck by, for example, a piece of machinery.

Figure 8:
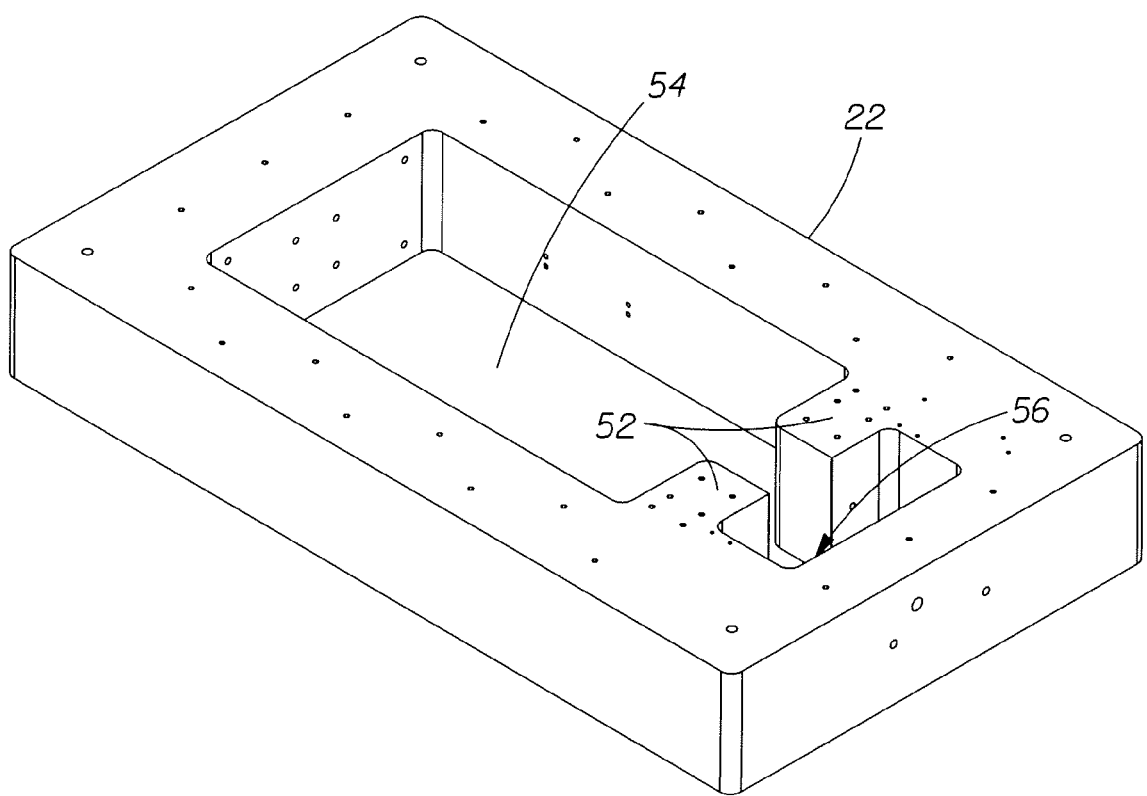
FIG. 8 is a perspective view of a base of a press in accordance with an embodiment of the present invention.

Referring to FIGS. 5A and 8, base 22 may be mounted, including securely mounted, on top of support air bags 24, or more particularly, top plates 44. Base 22, in an embodiment, may be heavy and rigid, or stiff or inflexible, such that it has a high inertia. In some embodiments, base 22 may be substantially heavy and rigid. In certain embodiments, base 22 may be heavy and rigid in comparison to some of the other components of press 20. For example, base 22 may be about twice as heavy and/or rigid as some of the other components of press 20, about three times as heavy and/or rigid as some of the other components, about ten times as heavy and/or rigid as some of the other components, or any other suitable multiplicative nonzero value. As such, base 22 may provide further isolation, for example, from external and internal vibration, noise, etc. Similarly, base 22 may provide a stable structure that does not bend easily nor is affected by inertial or moment forces created by actuator 26 while press 20 is in operation. In certain embodiments, other components of press 20 may be as heavy and rigid as base 22. Base 22 may be any suitable weight or rigidity. In an embodiment, base 22 may be manufactured from steel, but it is recognized that base 22 could be manufactured from any number of materials, such as but not limited to any metal, plastic, graphite, etc., or any combination of materials. In a further embodiment, base 22 may include inlet areas 52, which may divide the open area into two sections, simulation area 54 and backplate air bag area 56.

Figure 9:
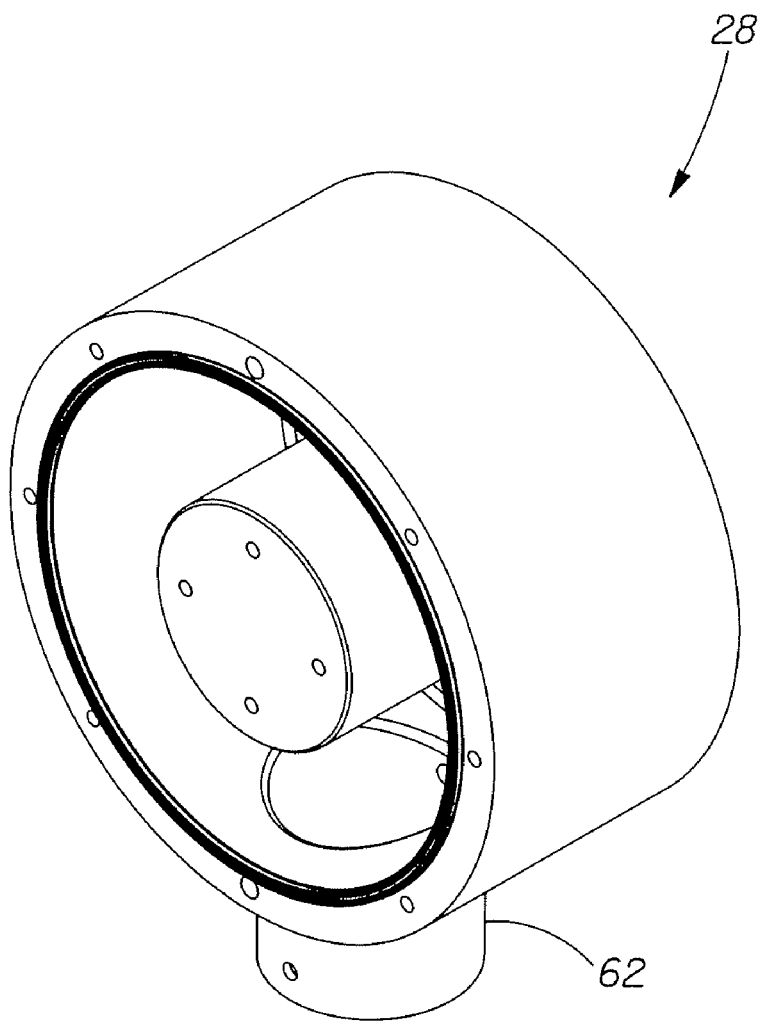
FIG. 9 is a perspective view of a back actuator support of a press in accordance with an embodiment of the present invention.
Figure 10:
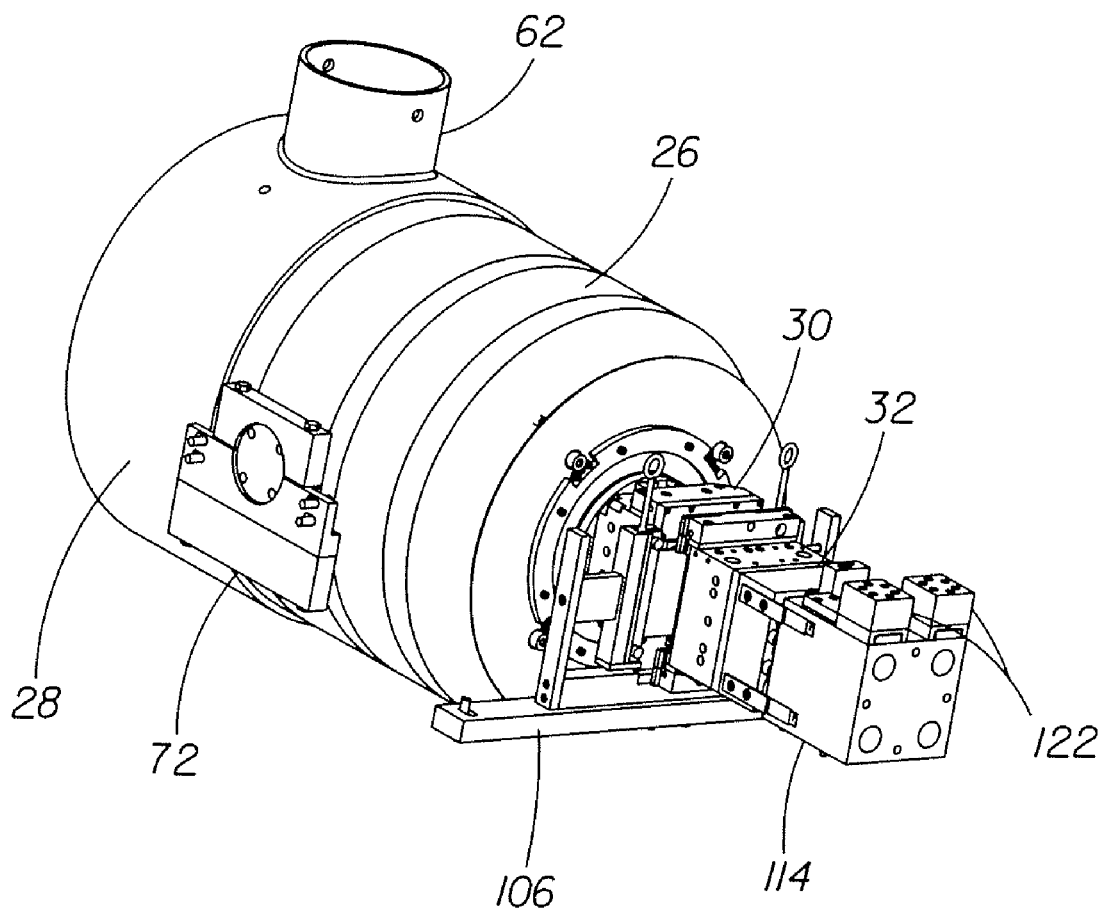
FIG. 10 is a perspective view of simulation components of a press in accordance with an embodiment of the present invention.

With reference now to FIGS. 5A, 9, and 10, back actuator support 28 may be mounted to base 22 and actuator 26, such that back actuator support 28 may be mounted between base 22 and actuator 26. Back actuator support 28 may provide strength and rigidity to actuator 26. Back actuator support 28, in an embodiment, may include an exhaust 62, which may further be connected to an exhaust system or fan to draw heat away from actuator 26. It is recognized that back actuator support 28 may be excluded in some embodiments of press 20.

Figure 11A:
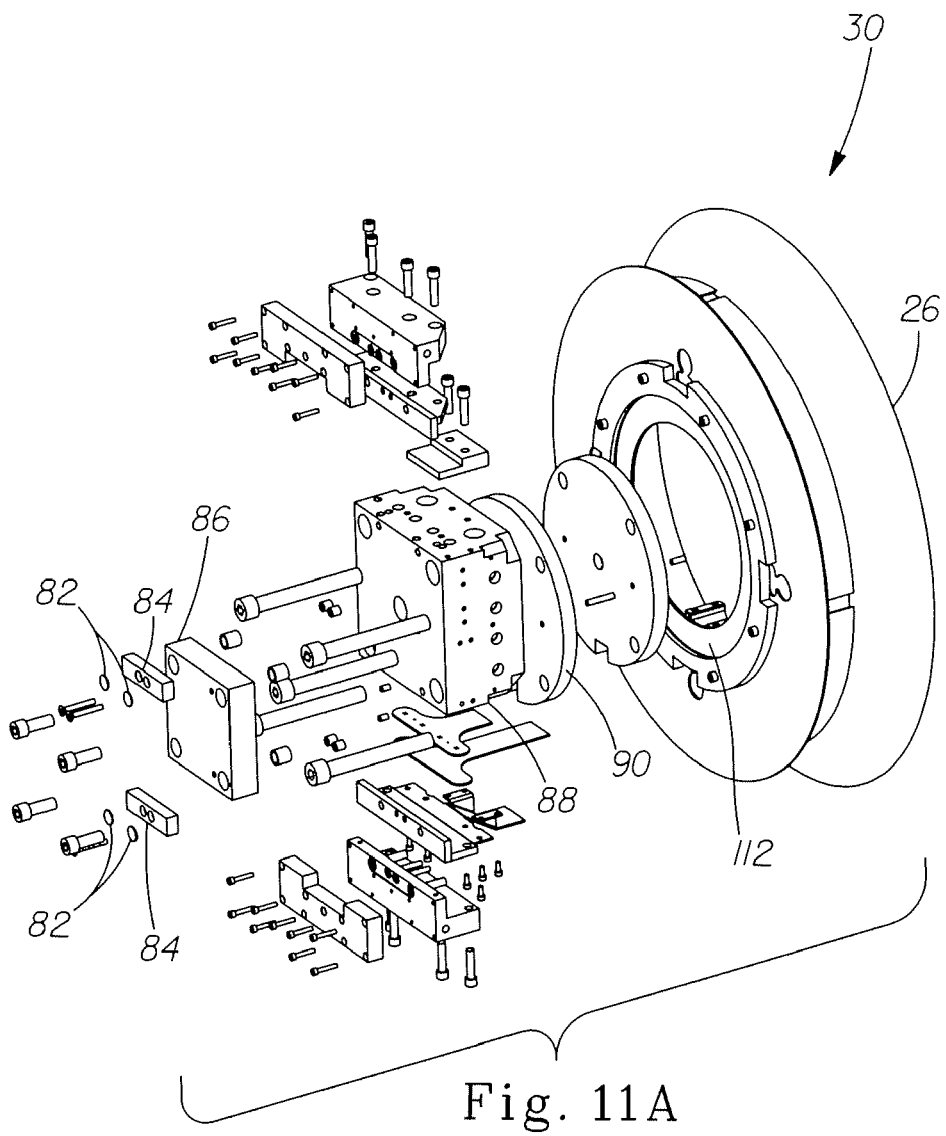
FIG. 11A is an exploded view of a moving plate assembly of a press in accordance with an embodiment of the present invention.

As shown in FIG. 10, in an embodiment, actuator 26 may be attached to base 22 using trunion block support 72. Actuator 26 may comprise a housing and a forward moving face 112, as shown in FIG. 11A, on which moving plate assembly 30 may be attached. In a further embodiment, actuator 26 may be a voice-coil type vibration exciter, e.g., an electrodynamic shaker system. It is recognized, however, that other suitable actuator systems, such as, but not limited to, a slider crank mechanism, a linear motor, or hydraulics, may be used in place of a voice-coil type vibration exciter. Actuator 26, in an embodiment, may further be designed for high bandwidth control. In certain embodiments, the armature structure of actuator 26 may be designed not to have any structural resonances within the bandwidth of the actuator control system and data collection system.

Actuator 26 may further include a sensor, such as a linear encoder or other suitable encoder, that measures the relative position of the armature, e.g., forward moving face 112, of the actuator relative to the housing of the actuator 26. The sensor, in one embodiment, may be used for real-time position feedback control during a cycle of the actuator 26.

As previously stated, actuator 26 may be positioned generally axially on a longitudinal axis of symmetry of base 22. The longitudinal axis, in some embodiments, may be located generally equidistant from a top and bottom surface of base 22 and generally equidistant from side surfaces of base 22. That is, the longitudinal axis of symmetry may be located generally along a central, longitudinal axis of base 22. In other words, actuator 26 may be positioned generally in the same plane as base 22.

Motion of certain portions of press 20 may cause errors in the measured force and may also result in discrepancies in gap measurement. Therefore, in some embodiments, actuator 26 may be positioned generally axially on a longitudinal axis of symmetry of base 22 such that the bending forces, e.g., inertial and/or moment forces, have less effect on press 20 while press 20 is in operation than would exist if actuator 26 were not positioned generally axially on a longitudinal axis of symmetry of base 22. In some embodiments, actuator 26 may be positioned generally axially on a longitudinal axis of symmetry of base 22 such that no bending forces of press 20 exist. Thus, in some embodiments, bending forces of press 20 may be neglected during operation of press 20. That is, bending forces of press 20 may be reduced or may not exist, and so need not be considered, when determining the effects of a process on a workpiece.

Figure 11B:
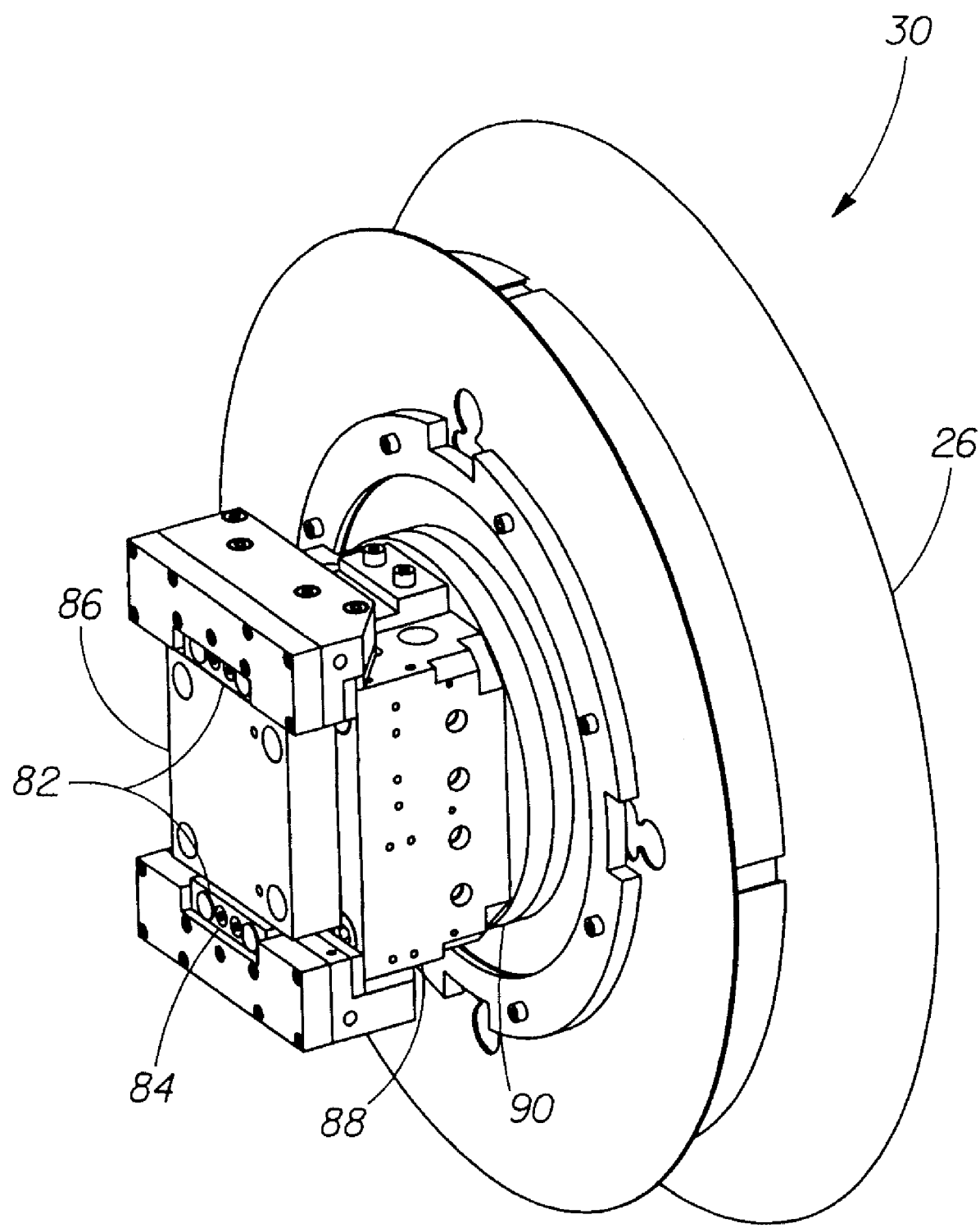
FIG. 11B is a perspective view of a moving plate assembly of a press as shown in FIG. 11A.

Reference now is made to FIGS. 10, 11A, and 11B. FIG. 11A shows an exploded view of an embodiment of the components of moving plate assembly 30, while FIG. 11B shows the components together. Moving plate assembly 30 may include an insulating plate 90 mounted to forward moving face 112 of actuator 26 and heating/cooling block 88, such that the insulating plate 90 is between forward moving face 112 and heating/cooling block 88. Insulating plate 90 may insulate actuator 26 from the varying temperatures of heating/cooling block 88.

In some embodiments, the temperature of heating/cooling block 88 and heating/cooling block 98 (see FIGS. 10, 12A, and 12B) may be controlled, and in other embodiments they may be independently controlled. In an embodiment, glycol lines may be connected to heating/cooling block 88 to decrease the temperature of heating/cooling block 88. Alternatively, liquids or refrigerants other than glycol can be used. Similarly, it is recognized that any suitable means of cooling heating/cooling block 88 may be used to decrease the temperature of heating/cooling block 88, including but not limited to air cooling by circulating air through heating/cooling block 88, etc. In an embodiment, heating cartridges may be placed in heating/cooling block 88 to increase the temperature of heating/cooling block 88. Alternatively, it is recognized that any suitable means of heating heating/cooling block 88 may be used to increase the temperature of heating/cooling block 88. Heating/cooling block 88 may further include temperature sensors or thermocouples that measure the temperature of heating/cooling block 88. Therefore, the temperature of heating/cooling block 88 can be increased or decreased automatically using drive controller 200 or an independent control system to maintain a desired temperature throughout simulation.

Tooling plate 86 may be mounted to heating/cooling block 88. Alternatively, tooling plate 86 may be integral with heating/cooling block 88. Tooling plate 86 may provide the simulated surface of one of the compression rolls 12 or 14 shown in FIG. 1. Tooling plate 86, in one embodiment, may be interchangeable and may be changed, as desired, to simulate different deformation processes, such as activation, fusion bonding, embossing, crimping, etc. FIGS. 11A and 11B illustrate tooling plate 86 as having a substantially planar surface. Tooling plate 86 may, however, include a protuberance, a pattern, a plurality of protuberances or patterns, depressions, grooves, etc., or any other characteristic that is desired for simulation. In an embodiment, tooling plate 86 includes a nub. A nub may be any desired size, including any nonzero size, or from about 0.1 mm to about 50 mm or larger, or from about 1 mm to about 10 mm, or about 2 mm, etc.

Moving plate assembly 30 may include target blocks 84 mounted to heating/cooling block 88. In an embodiment, target plates 82 may be mounted to target blocks 84 for use in conjunction with optical position sensors 92 of backplate assembly 32. Target plates 82 may be reflecting mirrors. In embodiments, target plates 82 may be used in conjunction with capacitive position sensors rather than optical position sensors 92. Alternatively, other types of sensors may be used, such as, but not limited to, eddy current sensors, etc. Target plates 82 and sensors 92 may measure the gap between tooling plates 86 and 100. The sensors 92 may measure the gap between tooling plates 86 and 100 during each cycle of actuator 26. The gap data may be used, in addition to generating material stress-strain characteristics, to update the command given to the real-time position control loop (which may use the linear encoder for real-time position feedback) for the next cycle. The feedback gap data from sensors 92 may be used to adjust the next cycle for deviations between the gap measurement and the armature position measured with the linear encoder.

As previously mentioned, it is recognized that not all components described in detail need be provided with all embodiments of press 20. For example, insulating plate 90, heating/cooling block 88, glycol lines, heating cartridges, tooling plate 86, target blocks 84, target plates 82, etc. may be excluded or altered, and the resulting press will remain in accordance with an embodiment of press 20 of the present invention.

Figure 12A:
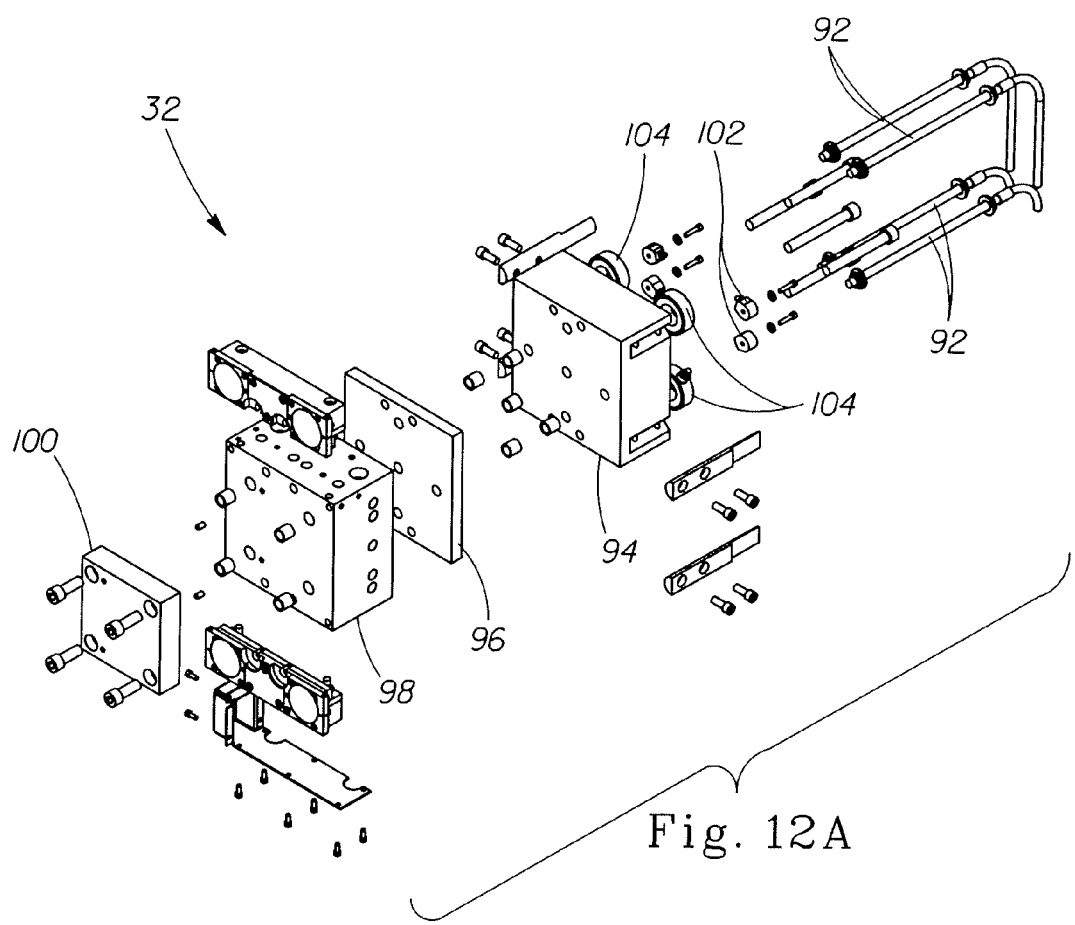
FIG. 12A is an exploded view of a backplate assembly of a press in accordance with an embodiment of the present invention.
Figure 12B:
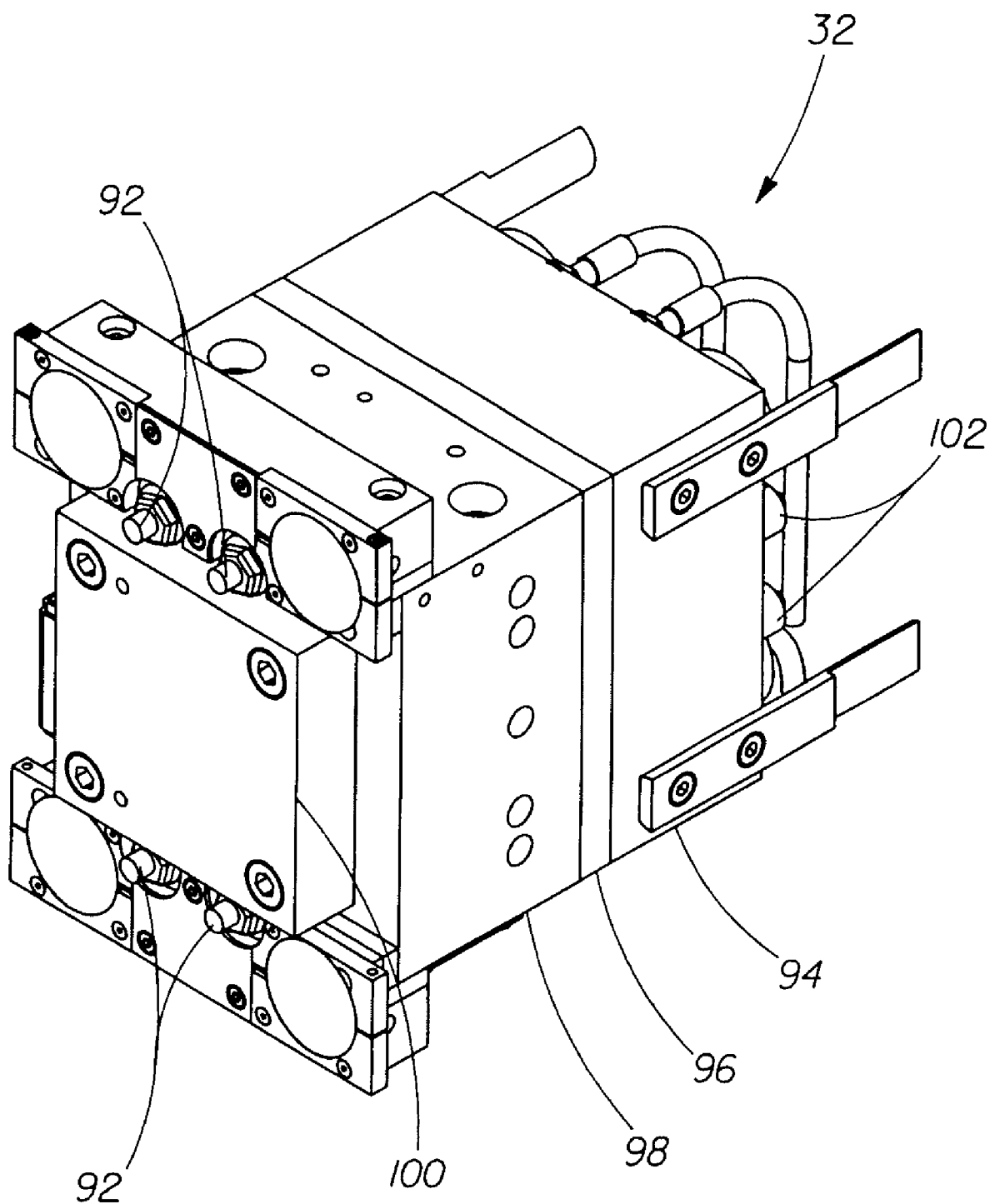
FIG. 12B is a perspective view of a backplate assembly of a press in as shown in FIG. 12A.

Reference now is made to FIGS. 10, 12A, and 12B. FIG. 12A shows an exploded view of an embodiment of the components of backplate assembly 32. FIG. 12B shows the components together. Backplate assembly 32 may include position sensors 92. As previously discussed, position sensors 92 may be capacitive sensors, optical sensors, eddy current sensors, etc. In an embodiment as illustrated in FIGS. 12A and 12B, position sensors 92 may be optical sensors used in conjunction with target plates 82 (e.g., reflective mirrors) to measure the gap between tooling plates 86 and 100.

Load cells 104 and accelerometers 102 may be mounted to support block 94. Load cells 104 and accelerometers 102 may contribute to active gap control. For example, in some embodiments, gap measurement, the distance between tooling plate 86 and 100, may not be compensated to calculate the actual gap simulated by press 20 by measuring the movement of backplate assembly 32 and subtracting the movement from the gap measurement. In some embodiments, under dynamic conditions, inertial accelerations and forces may not be neglected. Load cells 104 may measure the reaction force or support force applied to backplate assembly 32. This reaction force is generally equal to the actual force applied to the workpiece/web material only if there is no acceleration of backplate assembly 32. If there is acceleration of the backplate assembly 32, the reaction force measured by load cells 104 may differ from the actual force applied to the workpiece/web material by an amount equal to the inertial force causing the acceleration of the backplate assembly 32. Accelerometers 102 may measure the acceleration of backplate assembly 32. The inertial force may be determined by multiplying the acceleration measured by accelerometers 102 by the mass of backplate assembly 32. The actual force applied to the workpiece/web material may be obtained by adding the inertial force to the reaction force measured by load cells 104.

Therefore, press 20 may be suitable for active gap control. That is, press 20 may be used to measure the force applied to the workpiece/web material in a manner that includes the forces experienced by the workpiece/web material while the forces from external loads, including but not limited to, inertial loads from the equipment, vibration from sources external to the press, etc. are filtered. In some embodiments, the dynamic gap, i.e., the gap measured at any point in time during operation of press 20, may be measured to a level of accuracy that is an order of magnitude greater than gap values that may be experienced by workpiece/web materials during the actual process that is being simulated by press 20. For example, press 20 may measure the dynamic gap during simulation to an accuracy of generally about 1 μm.

Insulator plate 96 may be mounted to support block 94 and heating/cooling block 98, such that insulator plate 96 may be mounted between support block 94 and heating/cooling block 98. Insulator plate 96 may insulate load cells 104 and accelerometers 102 from the varying temperatures of heating/cooling block 98.

Similar to heating/cooling block 88, the temperature of heating/cooling block 98 may be controlled, including independently controlled. In an embodiment, glycol lines may be connected to heating/cooling block 98 to decrease the temperature of heating/cooling block 98. Alternatively, liquids or refrigerants other than glycol may be used. Similarly, it is recognized that any means of cooling heating/cooling block 98 may be used to decrease the temperature of heating/cooling block 98, such as air cooling by circulating air through heating/cooling block 98, etc. In an embodiment, heating cartridges may be placed in heating/cooling block 98 to increase the temperature of heating/cooling block 98. Alternatively, it is recognized that any technique for heating heating/cooling block 98 may be used to increase the temperature of heating/cooling block 98. Heating/cooling block 98 may further include temperature sensors or thermocouples that measure the temperature of heating/cooling block 98. Therefore, the temperature of heating/cooling block 98 can be increased or decreased automatically using drive controller 200 or an independent control system to maintain a desired temperature throughout simulation.

Tooling plate 100 may be mounted to heating/cooling block 98. Alternatively, tooling plate 100 may be integral with heating/cooling block 98. Tooling plate 100 may provide the simulated surface of one of the compression rolls 12 or 14, shown in FIG. 1. Typically, the compression roll simulated by tooling plate 100 will be the opposite roll than is simulated by tooling plate 86 of moving plate assembly 30. Tooling plate 100 may be interchangeable and may be changed, as desired, to simulate different deformation processes, such as activation, fusion bonding, embossing, crimping, etc. FIGS. 12A and 12B illustrate tooling plate 100 as having a substantially planar surface. Tooling plate 100 may, however, include a protuberance, a pattern, a plurality of protuberances or patterns, or any other characteristic that is desired for the simulation.

In an embodiment, tooling plate 100 may be substantially planar. Tooling plate 100 may simulate a smooth, flat, or blank compression roll, i.e., an anvil roll, such as roll 14 shown in the nip process of FIG. 1. Either, or both, tooling plate 86 or 100 may provide a surface having a protuberance, a pattern, a plurality of protuberances or patterns, etc., or may provide a smooth, flat surface. That is, either tooling plate 86 or 100 may provide a surface for simulating any type of process, such as activation, fusion bonding, embossing, crimping, etc. Similarly, either tooling plate 86 or 100 may provide a surface simulating an anvil roll. Tooling plates 86 and 100 may, in an embodiment, provide the same or substantially similar surfaces. Alternatively, tooling plates 86 and 100 may provide generally dissimilar surfaces.

Again, it is recognized that not all components described in detail need be provided with all embodiments of press 20. For example, position sensors 92, load cells 104, accelerometers 102, insulator plate 96, heating/cooling block 98, glycol lines, heating cartridges, tooling plate 100, etc. may be excluded or altered, and the resulting press will remain in accordance with an embodiment of press 20 of the present invention.

Figure 13:
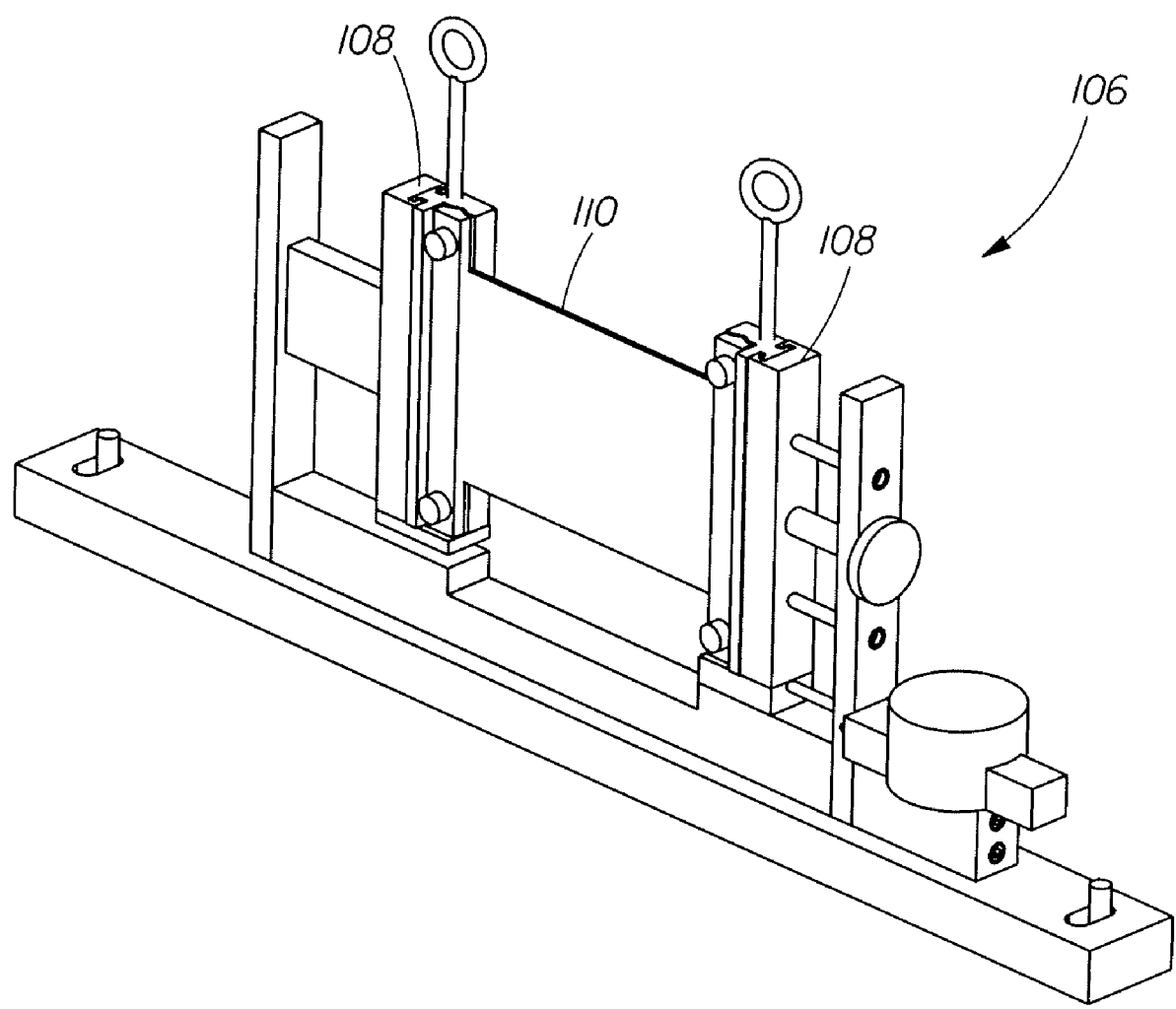
FIG. 13 is a perspective view of a material holder of a press in accordance with an embodiment of the present invention.

Material holder 106 may be removably located between moving plate assembly 30 and backplate assembly 32, as shown in FIG. 10. With reference to FIG. 13, material holder 106 may generally include material clips 108 which may hold the ends of material sample 110. Material holder 108 may be positioned such that material clips 108 hold material sample 110 between tooling plate 86 of moving plate assembly 30 and tooling plate 100 of backplate assembly 32. In a production line process, different workpiece/web materials can exhibit different stress or strain characteristics as they are moved through rolls, such as rolls 12 and 14. Similarly, different processes, such as activation, fusion bonding, embossing, crimping, and the like, may submit workpiece/web materials to different stresses and strains. In other words, the workpiece/web materials traveling through rolls 12 and 14 in a nip type process, for example, can exhibit different extents of stretching as they are passed between rolls 12 and 14. The amount of in-plane loading on the workpiece can influence both the stress/strain of the material during the deformation process and the resulting final state of the material after the process is completed. As such, the material holder 106 may be designed to apply in-plane stress/strain to the material sample 110. In one embodiment, to create the ability to simulate these differing stresses and strains of the workpiece/web materials, material clips 108 may be movable, such that any strain or stress can be applied to material sample 110.

Figure 14:
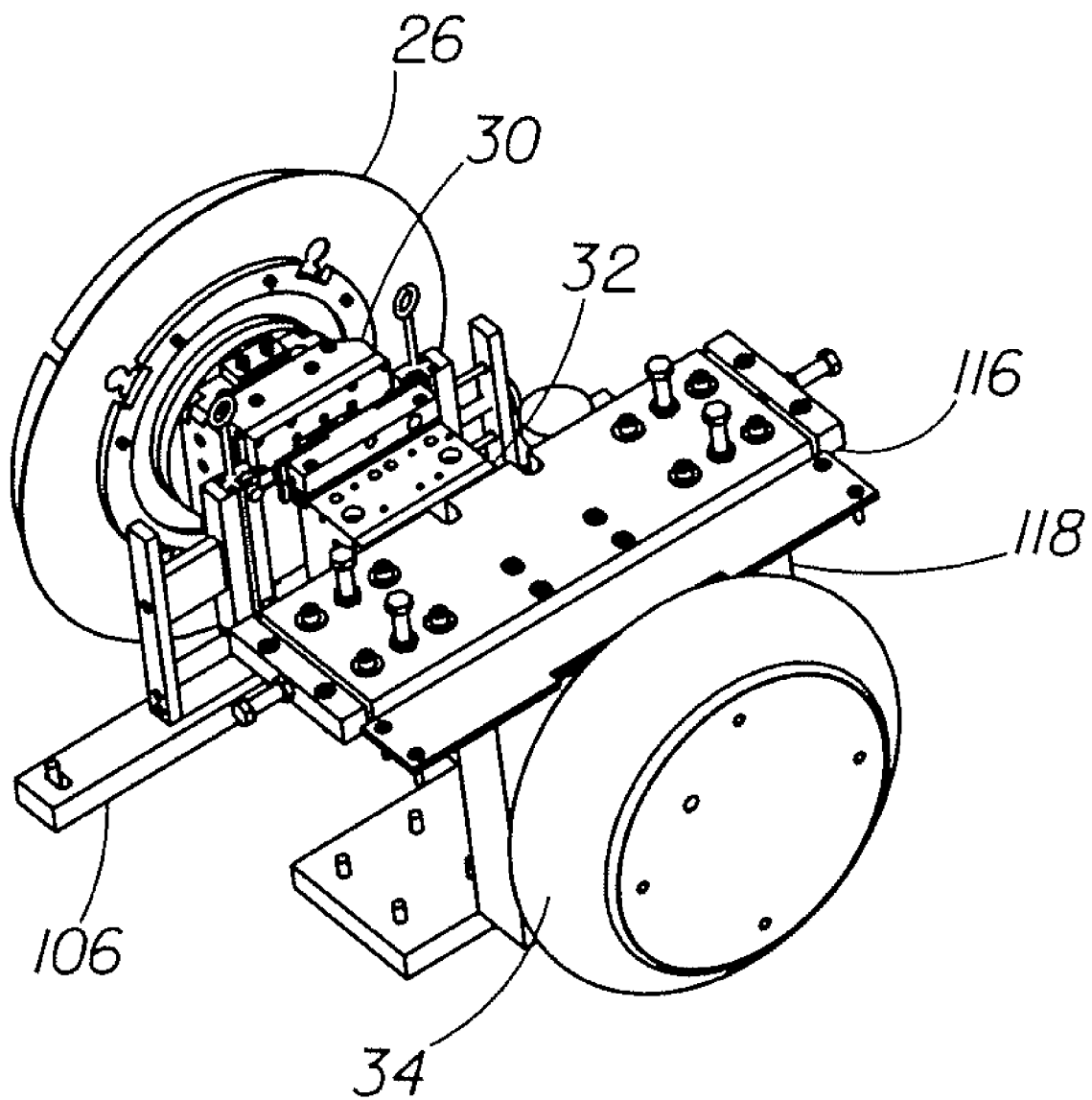
FIG. 14 is a perspective view of simulation components of a press in accordance with an embodiment of the present invention.

As can be seen in FIGS. 6, 10, and 14, backblock 114 may be attached to the back of backplate assembly 32. Backblock 114 may further be attached to upper girdle 116. In an embodiment, linear bearings 122 may be used to attach backblock 114 to upper girdle 116. Linear bearings 122, in a further embodiment, may be provided to permit backplace assembly 32 and backblock 114 to move in a linear direction, should something happen that is undesirable or unexpected. Upper girdle 116 may further be mounted to the inlet areas 52 of base 22 to provide further support, strength, and rigidity for backplate assembly 32. As such, backblock 114 may be positioned in the area between inlet areas 52. In a further embodiment, a second girdle plate may be located on the underneath side of base 22 and attached to inlet areas 52 and backblock 114 and may provide further support. One or more of backblock 114, upper girdle 116, and linear bearings 122 may be omitted from some embodiments of press 20.

Figure 15:
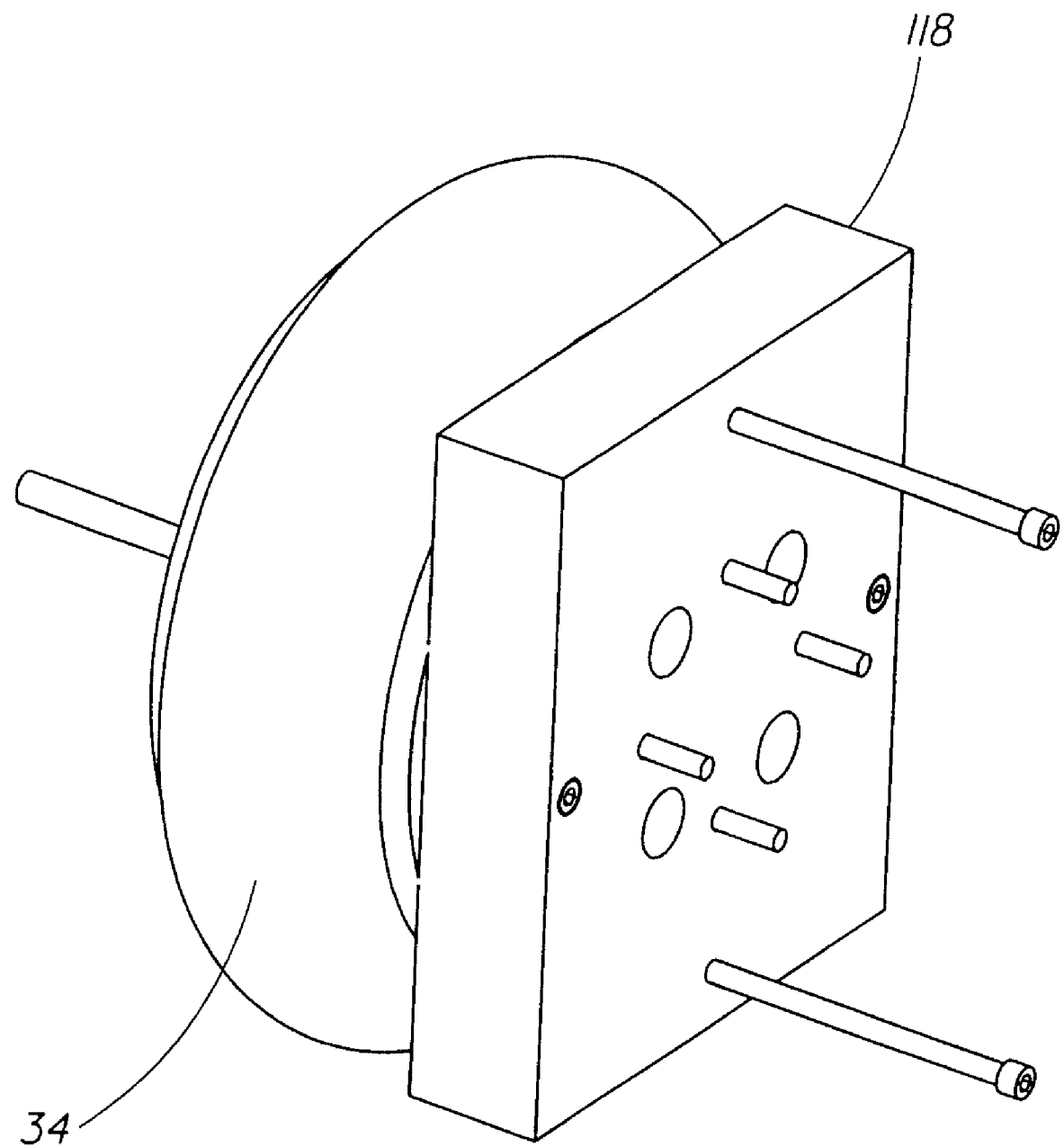
FIG. 15 is a perspective view of a safety release plate and backplate air bag of a press in accordance with an embodiment of the present invention.

Backblock 114 may be further attached to safety release plate 118. Safety release plate 118 may be mounted to backplate air bag 34, as illustrated in FIG. 15. Safety release plate 118 and backplate air bag 34 may be positioned in backplate air bag area 56 of base 22. Backplate air bag 34 may provide preload to keep safety release plate 118 firmly and rigidly held in position against inlet areas 52 unless potentially damaging forces are applied to the backplate assembly 32, in which case the backplate air bag 34 may allow the backplate assembly 32 to deflect, possibly preventing damage to press 20 components. Alternatively, in some embodiments, press 20 need not include safety release plate 118 nor backplate air bag 34.

Drive controller 200 may be provided for controlling the operation of actuator 26. In some embodiments, a suitable drive controller may be a personal computer with suitable hardware and programming. It is recognized that any suitable controller may be used for controlling the operation of actuator 26. In an embodiment, more than one controller may be suitable or desirable to control the operation of actuator 26. Similarly, one or more controllers may be provided to control the operation of other components of press 20, including but not limited to heating/cooling blocks 88 and 98, sensors 92, etc. Alternatively, drive controller 200 may control the operation of all components of press 20.

Figure 18:
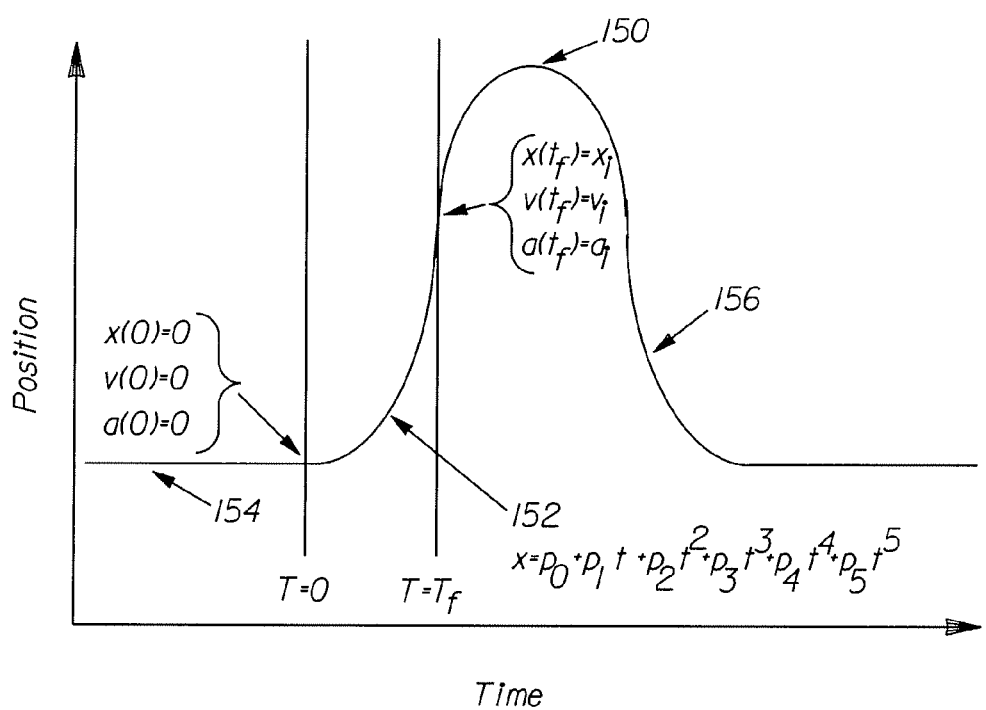
FIG. 18 is a graph of the trajectory motion profile for a press in accordance with an embodiment of the present invention.

In an embodiment, there may be multiple segments of a motion trajectory profile for press 20 of the present invention (see FIG. 18). A Rotary motion profile segment 150 may represent the engagement state of moving plate assembly 30 with the workpiece W. An Approach profile segment 152 may represent the transition from the at-rest, retracted state of moving plate assembly 30 to the engagement state. A Stationary profile segment 154 may represent the at-rest, retracted state of moving plate assembly 30. In an embodiment, rotary motion profile 150 need only be maintained while tooling plate 100 is in contact with, or engages, the workpiece W. Equations and calculations that may be used for determining rotary motion profile 150 are described below.

Figure 16A:
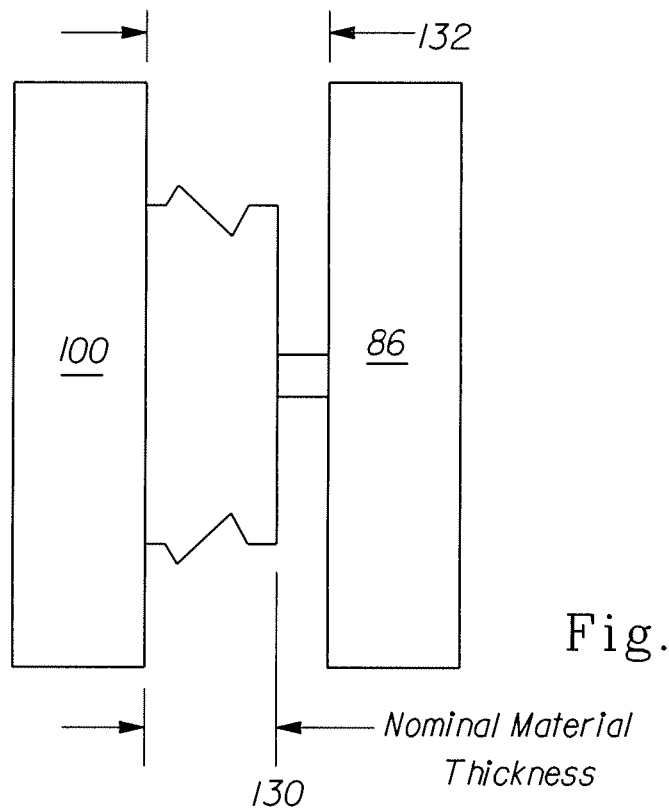
FIG. 16A is a side view of an embodiment of tooling plates of a press in accordance with an embodiment of the present invention during engagement of a fusion or bonding type operation.
Figure 16B:
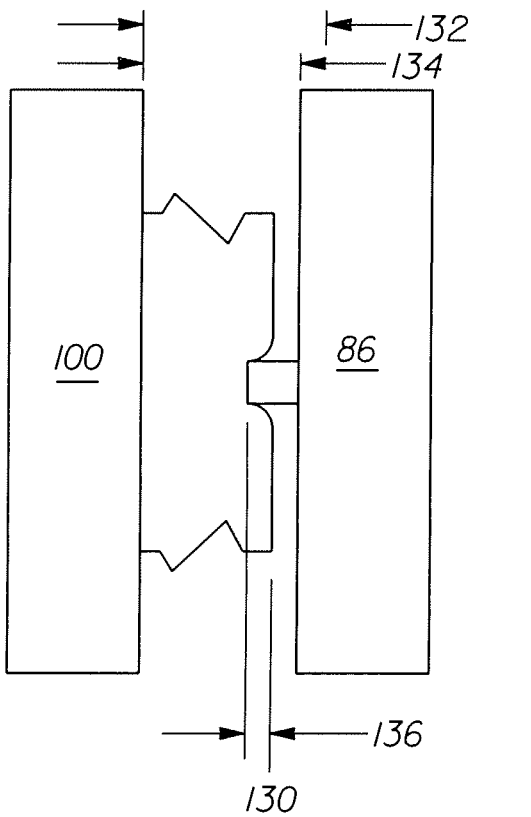
FIG. 16B is a side view of an embodiment of tooling plates of an embodiment of a press in accordance with an embodiment of the present invention during engagement of a fusion or bonding type operation.

The engagement of a protuberance 16 and a corresponding section 14a of the engaging or second roll 14, as it may be simulated by an embodiment of the press of the present invention, may be defined differently depending on the type of process, e.g., fusion bonding, crimping, cutting, activation/ring rolling, channel embossing, etc, that is being simulated. For example, during simulation of an embossing or bonding type operation, engagement may be defined in the following manner. The nominal thickness of a workpiece W may be determined or provided. As illustrated in FIGS. 16A and 16B, a plane of zero engagement 130 can be determined by moving tooling plate 86 forward in a very slow manner, so that no acceleration or vibrations in backplate assembly 32 are excited, until tooling plate 86, or a protuberance located on tooling plate 86, just touches tooling plate 100. Touching of tooling plate 86, or a protuberance thereon, and tooling plate 100 may be determined by a deviation of zero in the force measurement from load cells 104 in backplate assembly 32. Once touching occurs, the plane of zero engagement 130 can be readily determined using the nominal thickness of workpiece W, by moving a distance equal to the nominal thickness of workpiece W from the plane of tooling plate 100. Engagement may then be defined as:

$$E(t) = d_0 - d(t)$$

where E(t) 136 is the position of the protuberance during the engagement of tooling plate 86 and workpiece W at time t; $d_0$ 132 is the distance for zero engagement; and d(t) 134 is the distance of engagement at time t.

The actual engagement, in some embodiments, may include the change in dimension of the protuberance parallel to the direction of motion. Since the dimensional change might not be measured during the process, the control algorithm may not take the change into account. However, the dimensional change may be included during the post-processing of the engagement data from the force engagement curve. For a given force at time t and engagement E(t), the dimensional change (assuming, for purposes of an exemplary illustration, the protuberance is considered a simple vertical column and the loading does not exceed the elastic limit of the material that makes up the protuberance) may be estimated to be:

$$\Delta_{armature\text{-}plate}(t) = \frac{F(t)H_0}{A_0 E}$$

where $\Delta_{armature\text{-}plate}(t)$ is the dimensional change of the protuberance in the direction of engagement; F(t) is the material force; $H_0$ is the height or initial dimension of the protuberance in the direction of engagement; $A_0$ is the cross-sectional area of the protuberance; and E is the elastic modulus of the protuberance. If the shape of the protuberance is complex and the loading is expected to exceed the elastic limit of the material that makes up the protuberance, the change in the dimension can be determined using numerical/computational means, such as finite element analysis ("FEA"). Similarly, the actual engagement may include the change in dimension of tooling plate 100 parallel to the direction of motion, i.e., $\Delta_{back\text{-}plate}(t)$. In one embodiment, the change in dimension may be determined using numerical/computational means, such as FEA. Once the change in protuberance height and the dimension change in tooling plate 100 are known, the stored engagement data can be post-processed using the following equation:

$$E(t)_{actual} = E(t)_{measured} - \Delta_{armature\text{-}plate}(t) - \Delta_{back\text{-}plate}(t)$$

Figure 17A:
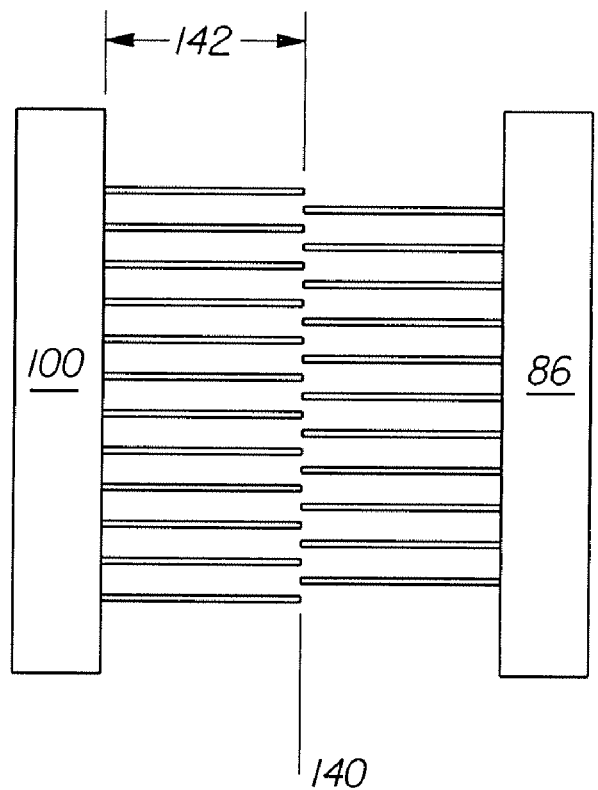
FIG. 17A is a side view of another embodiment of tooling plates of a press in accordance with an embodiment of the present invention during engagement of an activation type operation.
Figure 17B:
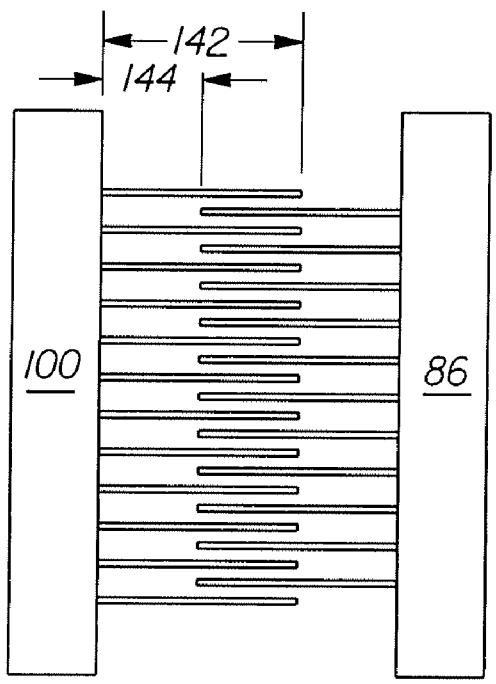
FIG. 17B is a side view of another embodiment of tooling plates of a press in accordance with an embodiment of the present invention during engagement of an activation type operation.

In another example, during simulation of an activation type operation, engagement may be defined in the following manner. The geometry of the plates and/or protuberances that may be provided on the plates may be known. As illustrated in FIGS. 17A and 17B, the plane of zero engagement 140 may be determined by offsetting the plane of tooling plate 100 by the height of the protuberances extending from tooling plate 100. As above, engagement may then be defined as:

$$E(t) = d_0 - d(t)$$

where E(t) 146 is the position of the protuberances during the engagement of tooling plate 86 and a workpiece at time t; $d_0$ 142 is the distance for zero engagement; and d(t) 144 is the distance of engagement at time t.

In an embodiment, during rotary motion profile 150, a point site $W_{PS}$ on a workpiece W, such as a web of material, moves at a velocity $V_W$ through a nip N defined by rolls 12 and 14 and may be engaged by a protuberance 16 and a corresponding section 14a of second roll 14 for a time period of 2T as it moves through the nip N. One-half of 2T, or T, is the time for protuberance 16 to reach the maximum depth of engagement. One-half of the total engagement time 2T that the given point site $W_{PS}$ on the workpiece W may be engaged by the protuberance 16 and the corresponding section 14a of second roll 14 can be determined by the following equation:

$$T = a\cos\left[1 - \frac{E_M}{D_i}\right] \cdot \left[\frac{D_i}{2V_W}\right]$$

where $E_M$ is the amount by which the point site $W_{PS}$ is compressed from an initial thickness $M_T$ to a compressed final thickness G by the protuberance 16 and the corresponding section 14a of second roll 14; $D_i$ is the diameter of the first and second rolls 12 and 14 (assuming, for an exemplary embodiment, that rolls 12 and 14 have the same diameter and that the lengths of the protuberances 16 are included in the diameter of roll 12); and $V_W$ is the workpiece velocity.

Using the equation for engagement time T, set out above, and the predefined values for the process to be simulated, drive controller 200 may determine the engagement time T, which is equal to one-half of the total time period 2T that a given point site $W_{PS}$ on a workpiece may be engaged by protuberance 16. The engagement position of a protuberance 16 may be determined by drive controller 200 using the following equation:

$$E(t) = E_M - D_i \cdot \left[1 - \cos\left[a\cos\left(1 - \frac{E_M}{D_i}\right) \cdot \left(\frac{t}{T} - 1\right)\right]\right]$$

where E(t) is the position of the protuberance during engagement; $E_M$ is the amount by which the point site $W_{PS}$ is compressed by the protuberance 16 and the corresponding section 14a of second roll 14 or the amount by which the point site $W_{PS}$ is compressed by a protuberance on tooling plate 86 and the surface of tooling plate 100; $D_i$ is the diameter of the first and second rolls 12 and 14 (assuming, for an exemplary embodiment, that that rolls 12 and 14 have the same diameter and that the lengths of the protuberances 16 are included in the diameter of roll 12); t is equal to 0 to 2T.

The velocity of the protuberance 16 at a given engagement position may be determined by taking the first derivative of the position value and may be represented by the following equation:

$$\frac{d}{dt}E(t) = -D_i \cdot \sin\left[a\cos\left(1 - \frac{E_M}{D_i}\right) \cdot \left(\frac{t}{T} - 1\right)\right] \cdot \left[\frac{a\cos\left(1 - \frac{E_M}{D_i}\right)}{T}\right]$$

Similarly, the acceleration of the protuberance 16 at a given engagement position of a protuberance may be determined by taking the second derivative of the position value and may be represented by the following equation:

$$\frac{d^2}{dt^2}E(t) = -D_i \cdot \cos\left[a\cos\left(1 - \frac{E_M}{D_i}\right) \cdot \left(\frac{t}{T} - 1\right)\right] \cdot \left[\frac{a\cos\left(1 - \frac{E_M}{D_i}\right)}{T}\right]^2$$

To complete the motion trajectory calculation, an approach curve may be calculated that transitions from the at-rest, retracted state 154 of the moving plate assembly 30 to the position, velocity, and acceleration state at the beginning of rotary motion profile 150, set forth above.

In an embodiment, it may be desirable for the overall trajectory to be smooth, as illustrated in FIG. 18. However, the displacement profile does not need to be rotary in nature. That is, the controller may be programmed to be linear, stepped, or approximately saw tooth, as illustrated previously in FIGS. 4A, 4B, and 4C, respectively. Discontinuities in the reference profile may cause spikes in control command, overloading/saturating of control system components, and/or reduce control accuracy. With this in mind, there are six boundary conditions that could be satisfied. The position, velocity, and acceleration at the beginning of approach profile segment 152 could match the position, velocity, and acceleration at the end of stationary profile segment 154, and the position, velocity, and acceleration at the end of approach profile segment 152 could match the position, velocity, and acceleration at the beginning of rotary motion profile segment 150. These boundary conditions may be satisfied by modeling approach profile segment 152 with a fifth order polynomial, in the form of:

$$x(t) = p_0 + p_1 t + p_2 t^2 + p_3 t^3 + p_4 t^4 + p_5 t^5$$

The first three boundary conditions, i.e., the position, velocity, and acceleration at the beginning of approach profile segment 152 (and the end of stationary profile segment 154), may, in an embodiment, be:

$$x(0)=0$$

$$v(0)=0$$

$$a(0)=0$$

since the moving plate assembly 30 is in an at-rest, retracted state. In some embodiments, these conditions can be satisfied by choosing the parameters:

$$p_0=0$$

$$p_1=0$$

$$p_2=0$$

In some embodiments, matching additional derivatives beyond velocity and acceleration may be desirable and beneficial.

The remaining three boundary conditions, i.e., the position, velocity, and acceleration at the end of approach profile segment 152 (and the beginning of rotary motion profile segment 154) may comprise the equations:

$$x(t_f)=x_i=p_3 t_f^3+p_4 t_f^4+p_5 t_f^5$$

$$v(t_f)=v_i=3p_3 t_f^2+4p_4 t_f^3+5p_5 t_f^4$$

$$a(t_f)=a_i=6p_3 t_f+12p_4 t_f^2+20p_5 t_f^3$$

where $x_i$ is the position at the initiation of the rotary motion profile 150; $v_i$ is the velocity at the initiation of the rotary motion profile 150; and $a_i$ is the acceleration at the initiation of the rotary motion profile 150. These equations may be expressed in matrix form:

$$\begin{Bmatrix} x_i \\ v_i \\ a_i \end{Bmatrix} = \begin{bmatrix} t_f^3 & t_f^4 & t_f^5 \\ 3t_f^2 & 4t_f^3 & 5t_f^4 \\ 6p_3 t_f & 12t_f^2 & 20t_f^3 \end{bmatrix} \begin{Bmatrix} p_3 \\ p_4 \\ p_5 \end{Bmatrix}$$

Solving the matrix for the polynomial coefficients, the following matrix equation is achieved:

$$\begin{Bmatrix} p_3 \\ p_4 \\ p_5 \end{Bmatrix} = \begin{bmatrix} t_f^3 & t_f^4 & t_f^5 \\ 3t_f^2 & 4t_f^3 & 5t_f^4 \\ 6p_3 t_f & 12t_f^2 & 20t_f^3 \end{bmatrix}^{-1} \begin{Bmatrix} x_i \\ v_i \\ a_i \end{Bmatrix}$$

The final parameter to select is $t_f$, which is the time for the moving plate assembly 30 to travel from the at-rest, retracted position 154 to the beginning of rotary motion profile segment 150. In an embodiment, the parameter $t_f$ may be selected to minimize the maximum velocity that moving plate assembly 30 achieves throughout approach profile 152. This may be done by evaluating the calculated approach profile 152 for a range of values for $t_f$ in time increments of the drive controller 200 integer sample rate or controller time step value and determining the maximum velocity for each value.

Figure 19:
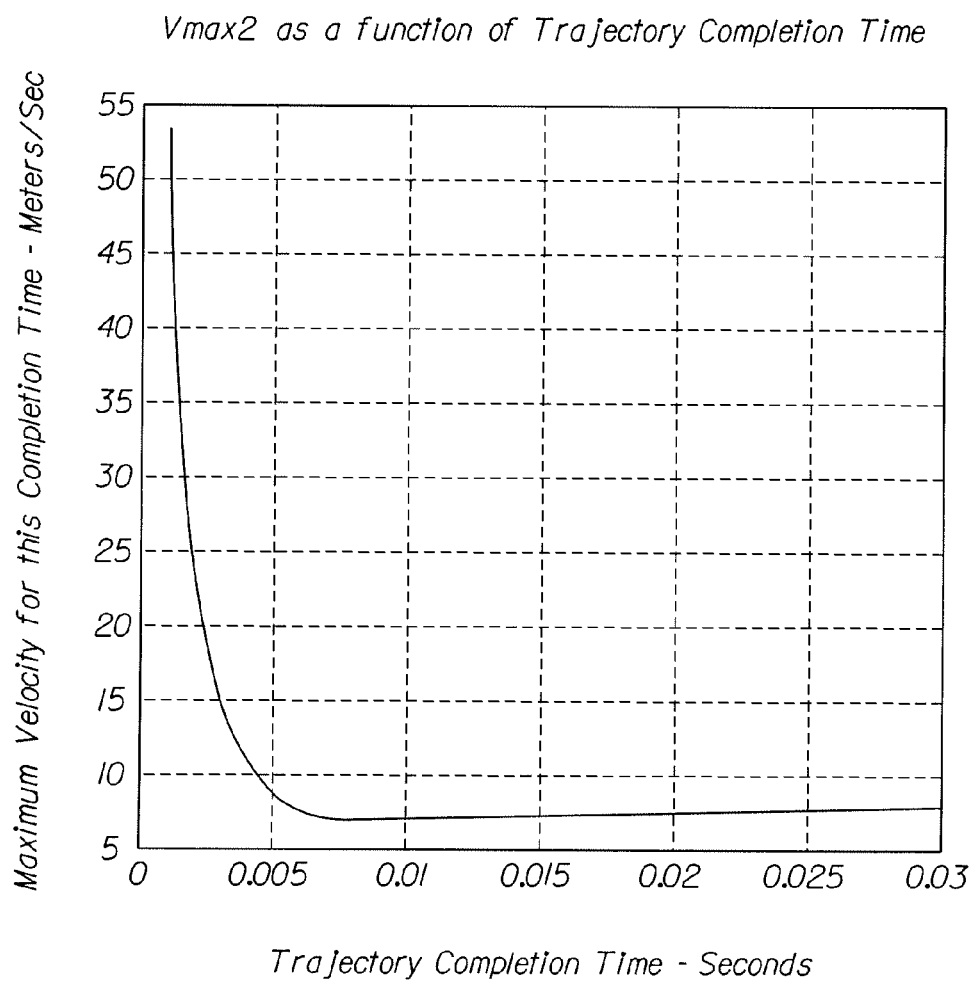
FIG. 19 is a graph of the variation in maximum velocity achieved in an approach profile as a function of the approach time for a press in accordance with an embodiment of the present invention.
Figure 20:
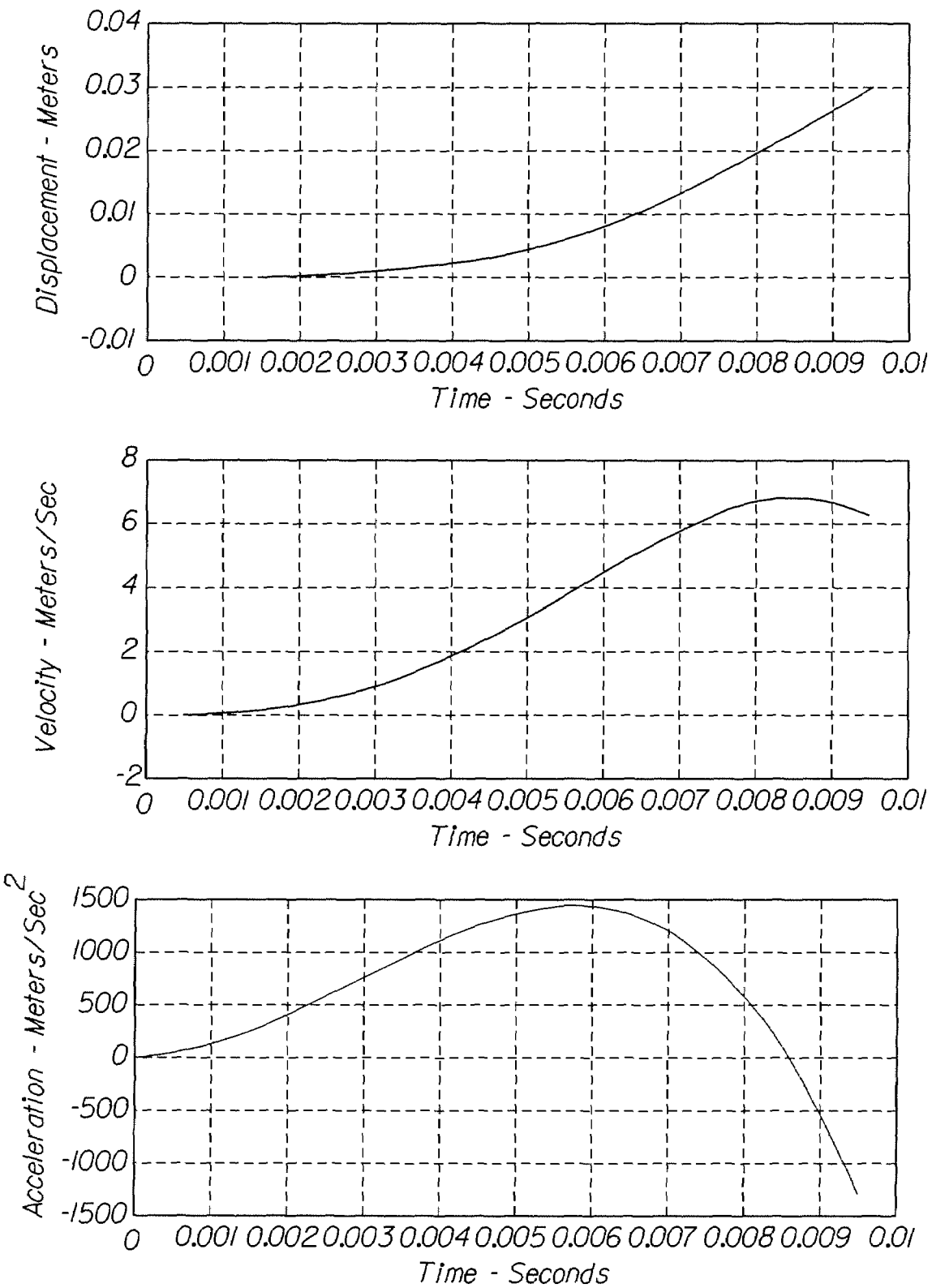
FIG. 20 is the resulting displacement, velocity, and acceleration curves for an approach profile for a press in accordance with an embodiment of the present invention.
Figure 21:
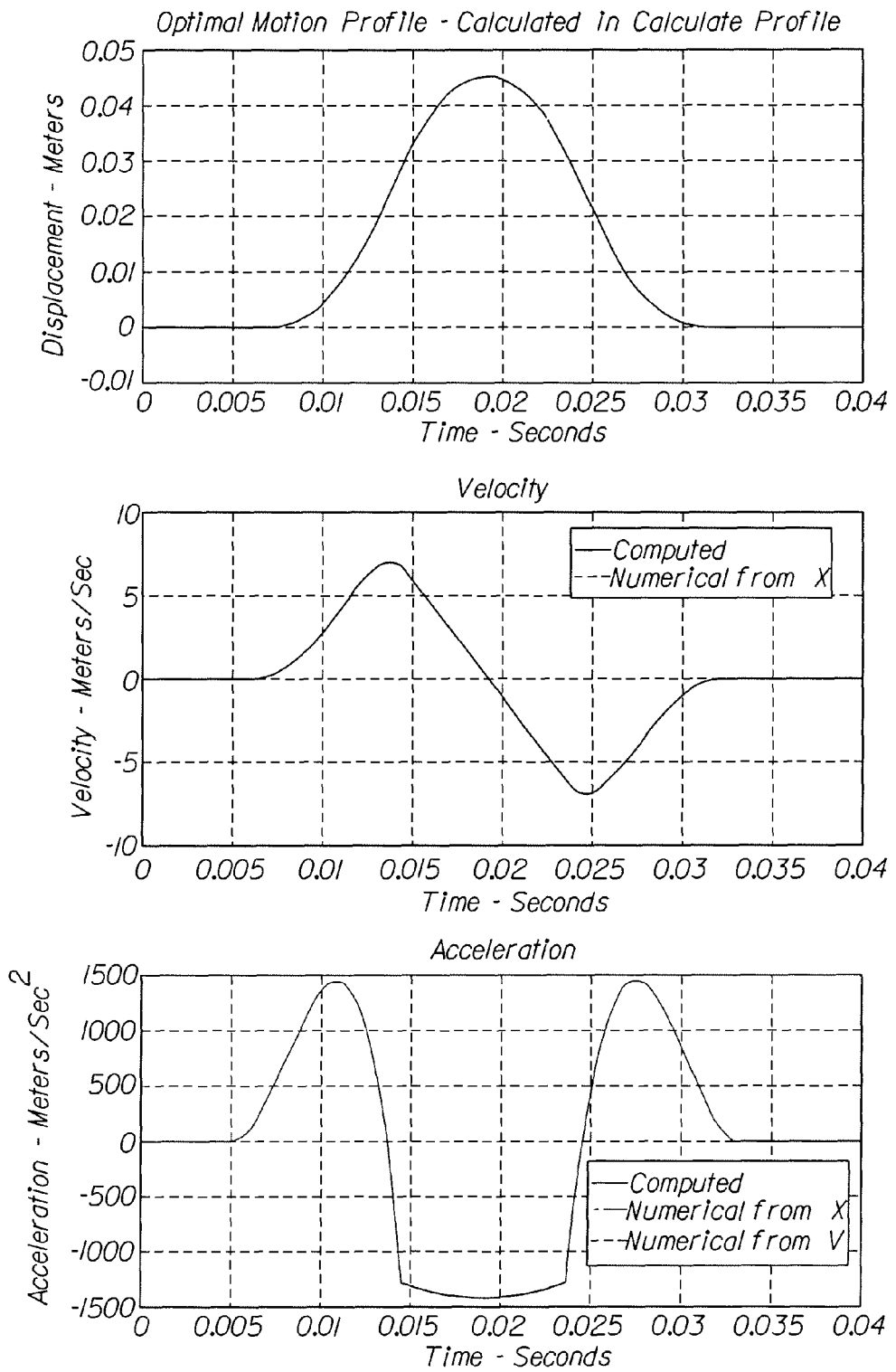
FIG. 21 is the resulting displacement, velocity, and acceleration curves for a complete trajectory motion profile for a press in accordance with an embodiment of the present invention.

FIG. 19 illustrates the variation in the maximum velocity achieved in approach profile 152 as a function of the approach time for an exemplary profile. The resulting approach profile displacement, velocity, and acceleration curves are illustrated in FIG. 20. The trajectory profile may be symmetric about the point of maximum extension of the moving plate assembly (i.e., the minimum gap between tooling plates 86 and 100). Therefore, retraction profile 156, shown in FIG. 18, may be identical to that of approach profile 152, although reversed with respect to time. However, it is recognized that retraction profile 156 need not be symmetrically identical to that of approach profile 152. The resulting displacement, velocity, and acceleration curves of the complete trajectory profile are shown in FIG. 21.

In an embodiment, a production line process, such as a nip type process, may be simulated by press 20 of the present invention in the following manner:

Prior to running a simulation, an engineer/technician may determine or may define one or more of the following parameters concerning the process to be simulated: a desired workpiece velocity $V_W$, i.e., the velocity at which the workpiece W would run if passed between a pair of first and second rolls 12 and 14; the diameter $D_i$ of the first and second rolls 12 and 14; and an amount $E_M$ by which a point site $W_{PS}$ is compressed by a first roll protuberance 16 and the corresponding section 14a of second roll 14, i.e., the workpiece initial thickness $M_T$ less the workpiece final thickness G.

Drive controller 200 may then determine the engagement time T using the equation for engagement time T, set out above, and the predefined values for the process to be simulated. Subsequently, using the result for engagement time T from the previous calculation, drive controller 200 may determine the engagement position, velocity, and acceleration for any given time t during the rotary motion profile segment, where the time t will, in an embodiment, typically range from 0 to 2T, as previously described.

Drive controller 200 may then determine an approach curve that transitions from the at-rest, retracted state 154 of the moving plate assembly 30 to the position, velocity, and acceleration state at the beginning of rotary motion profile 150. Similarly, drive controller 200 may determine a retraction profile 156. Again, the retraction profile 156, may be identical to that of approach profile 152, although reversed with respect to time. It is recognized that retraction profile 156 need not be symmetrically identical to that of approach profile 152.

Drive controller 200 may determine the initial press position control loop commands and iterative update of the commands to reduce profile error. In other embodiments, as previously mentioned, an independent controller may be used instead of controller 200. However, for purposes of illustration, controller 200 will be referenced in relation to the control loop. In an embodiment, a proportional, integral, differential ("PID") position feedback loop may be used for real-time control of the armature, e.g., forward moving face 112, position. The linear encoder signal, as previously described, may be used as the position reference feedback. The encoder may be low noise, high resolution. Furthermore, the encoder may have a measurement range that covers the entire range of motion of the armature. Controller 200 may be a very high speed and high gain system. In an embodiment, extremely accurate profile motion may be obtained by precise, iterative calculation of the closed loop, reference position commands utilized by controller 200.

In a system with a position loop having a perfect response, i.e., unity gain and zero phase, over the frequency bandwidth of the desired armature trajectory, the desired trajectory, as described above, may be the appropriate command for the position loop. However, where this is not the case, the loop command may be modified to achieve higher initial trajectory accuracy.

A frequency domain model may be utilized to calculate the position loop command. The press 20 may have an automatic-identification capability, which measures a frequency domain model of the press position loop characteristics comprising of a frequency response function ("FRF") between encoder response and position loop command.

A process to generate a valid FRF may be used to excite the system with an excitation signal that has energy across the entire frequency band of interest, and measure the excitation and response signals. The two signals may be transformed to the frequency domain using the fast Fourier transform ("FFT"). The complex ratio of phase and magnitude may be calculated between the two signals.

To reduce noise and improve the accuracy of the estimated FRF, an averaged, "H1" FRF may be calculated. The procedure for obtaining an averaged, "H1" FRF is now described. Multiple (N) time histories of excitation commands, $c_i(t)$, i=1, ... N, and associated encoder responses, $e_i(t)$, i=1, ... N, may be measured. These may be transformed via Fourier Transform to the frequency domain:

$$C_i(w) = \Im(c_i(t))$$

$$E_i(w) = \Im(e_i(t))$$

wherein w denotes the frequency, which ranges from 0 to ½ of the frequency at which the time data was sampled, and $\Im$ denotes the FFT. The averaged cross spectrum between the encoder response and input command may be calculated using the equation:

$$G_{ec}(w) = \frac{1}{N}\sum_{i=1}^{N} E_i(w)C_1^*(w)$$

wherein the '*' superscript indicates complex conjugate. The averaged power spectrum of the input command may be calculated using the equation:

$$G_{cc}(w) = \frac{1}{N}\sum_{i=1}^{N} C_i(w)C_1^*(w)$$

The FRF may be calculated as the ratio of the averaged cross spectrum and the averaged power spectrum:

$$H_{cc}(w) = \frac{G_{ec}(w)}{G_{cc}(w)}$$

The system response FRF, $H_{ec}$, calculated above, satisfies the relationship:

$$E(w) = H_{ec}(w)C(w)$$

The frequency domain representation of the command that may achieve a desired encoder profile can be calculated as:

$$C(w) = H_{cc}^{-1}(w)E(w)$$
$$= \frac{E(w)}{H_{cc}(w)}$$

If the desired time domain encoder profile is p(t), the command that will achieve that encoder profile may be calculated, within the limits of accuracy of the system response FRF and system noise, variation, and nonlinearity, as described below.

First, the desired time domain profile may be transformed to the frequency domain:

$$P(w) = \Im(p(t))$$

The frequency domain representation of the profile (or profile spectrum) may then be divided, on a frequency by frequency basis, by the system response FRF to calculate the desired frequency domain command:

$$C(w) = \frac{P(w)}{H_{cc}(w)}$$

The frequency domain command may then be inversely transformed to the time domain:

$$c(t) = \Im^{-1}(C(w))$$

When the press 20 has run a cycle, it may have the capability to examine the resulting profile error and update the command to reduce the error on the next cycle. In an embodiment, three operations may be performed, including command update to reduce error, merge encoder and optical sensor data to obtain desired gap error, and select and perform either fast or safe iteration updates.

The command update procedure, may be similar to the initial command calculation procedure described above. However, the command update procedure may operate on the profile error. Quantities of interest relating to the command update procedure may comprise the desired profile, p(t), the actual, measured profile, $p_m(t)$, the command, c(t), and the updated command, $c_u(t)$.

The profile error, $p_e(t)$, may be calculated as the difference of the desired profile and the measured profile:

$$p_e(t) = p(t) - p_m(t)$$

The profile error may be windowed with a window that has unity weighting over the rotary motion section of the profile and which smoothly transitions to zero at the ends of the profile. This can concentrate the control effort in the section of the profile that may be most important. An incremental change in the command, $\Delta c(t)$, may be calculated using the command calculation procedure described previously, but substituting the profile error for the desired profile. The updated command may then be calculated as the original command plus the change in command:

$$c_u(t) = c(t) + \Delta c(t)$$

Due to deflections that may occur in press 20 mechanical components at extremely high acceleration rates at which the press 20 may operate, the encoder and optical sensor readings may not agree exactly. Since the real-time position control loop may use the encoder as the reference feedback transducer, adjustments may be made in the encoder profile command in order to achieve the desired gap profile as measured by the optical gap sensors. This may be achieved by utilizing the optical sensor measurements to calculate the profile error.

Optical sensors 92 may have a maximum accurate measurement range. In an embodiment, optical sensors 92 may have a maximum accurate measurement range of about 15 mm. The total travel of the armature of the actuator 26 may extend beyond 15 mm. Therefore, in an embodiment, the optical sensor measurements and the encoder measurement may need to be stitched together, or combined.

In an embodiment, stitching of the measurements may be accomplished as follows. The optical sensor data may be truncated to the time interval from about 0.8 msec prior to, and 0.8 msec after, the cycle rotary profile begins and ends. The values of the encoder data and optical sensor data at the endpoints of the truncated time interval may be determined, and the offset between the data may be calculated. The optical sensor data may be low-pass filtered to determine endpoint values to minimize noise spikes at the endpoints that may introduce error in the offset determination. A linear slope may be added to the encoder data, so that it matches the amplitude of the optical sensor data at the time interval endpoints. In other embodiments, it is recognized that other suitable methods of combining the measurements, including other time intervals, may be utilized in accordance with the present invention.

In an embodiment, the press 20 may be run in a no-iteration mode or an iteration mode. In a no-iteration mode, no update of the command is performed. The iteration mode may further be broken into more than one iteration mode. For example, in one embodiment, the iteration mode may be further broken into a safe-mode-iteration and fast-iteration. In safe-mode-iteration, the command may be updated by a lower percentage than 100% of the calculated command update. For example, the command may be updated by 10%, 25%, 50%, 65%, 75%, 85%, or other suitable percentage of the calculated command update. Normally, -mode-iteration may be used when the actual profile is within the accuracy range required for the testing being conducted. In a further embodiment, in safe-mode-iteration, gradual updates to the command may be made which average the update over many cycles, thus, reducing the effect of random variables, such as material properties, electrical noise, etc.

Normally, safe-mode-iteration may be used to ensure the armature profile does not overshoot and cause tooling plates 86 and 100 (or protuberances thereon) to impact and possibly cause damage. If the profile gap is not within the accuracy range required for the testing being conducted, such as greater than 2 mm, for one example, fast-iteration may be used and the command may be updated with approximately 100% of the calculated command update, or other suitable percentage generally near 100%.

Prior to simulation, a workpiece/web material, or sample thereof, may be placed in material holder 106. As previously stated, to create the ability to simulate differing stresses and strains of the workpiece/web materials, material clips 108 of material holder 106 may be movable, such that any strain or stress can be applied to the workpiece/web material.

In an embodiment, simulation of a production line process and the effects of the process on the workpiece/web material may include simulating actual roll speeds, forces, cuts, perforations, bonds, etc. However, simulation of a production line process, in some embodiments, comprises simulating a wide range of roll speeds, forces, cuts, perforations, bonds, etc., including roll speeds, forces, cuts, perforations, bonds, etc. substantially near actual roll speeds, forces, cuts, perforations, bonds, etc. In some embodiments, any roll speeds, forces, cuts, perforations, bonds, etc. may be simulated using press 20 of the present invention. Additionally, in some embodiments, it may be desirable to perform a variety of material testing applications/modes including, but not limited to, simple compression, planar, simple shear, oscillatory viscoelasticity, etc. In further embodiments yet, the invention described herein may be used to simulate the shaking that a workpiece may experience during a production line process, such as folding.

In some embodiments, the invention described herein may be used to simulate combined multiaxial loading, such as differential roll surface speed, combined loading including compression and transverse shearing, and combined loading including compression and in-plane shearing. However, it is recognized that other combined multiaxial loading simulations may be performed using the various embodiments of the press described herein. In certain embodiments, the present invention may be used to measure and understand a material's mechanical response during various processes, as well as measuring a material's constitutive properties.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the invention have been illustrated and described, it would be obvious to those skilled in the art that various other changes and modifications can be made without departing from the scope of the invention. It is therefore intended to cover in the appended claims all such changes and modifications that are within the scope of this invention.

What is claimed is:

1. A simulation press comprising:
a main body;
an actuator attached to the main body such that the actuator is substantially axially aligned with a longitudinal axis of symmetry of the main body, the actuator having a moving face which moves generally in a straight line along the longitudinal axis of symmetry of the main body in the same plane as the main body;
a first plate operably coupled to the main body, the first plate being adapted to engage a workpiece;
a second plate operably coupled to the actuator for movement with a moving face of the actuator, the second plate being adapted to engage the workpiece; and
a drive controller coupled to the actuator for controlling the operation of the actuator in response to feedback from at least one feedback sensor so as to cause the second plate to move relative to the first plate such that the first and second plates engage at least one point site on the workpiece;
wherein at least one plate is able to be rotated, angled, or both rotated and angled.

2. The simulation press as set forth in claim 1, wherein the at least one feedback sensor comprises at least one sensor for measuring the position of the moving face of the actuator relative to a body of the actuator.

3. The simulation press as set forth in claim 1, wherein the at least one feedback sensor comprises at least one sensor for measuring the gap between the first plate and the second plate.

4. The simulation press as set forth in claim 3, wherein the drive controller alters the force generated within the actuator to control the motion of the moving face in response to feedback from the at least one sensor for measuring the gap between the first plate and the second plate.

5. The simulation press as set forth in claim 3, further comprising at least one sensor for measuring the position of the moving face of the actuator relative to a body of the actuator, wherein the drive controller alters the force generated within the actuator to control the motion of the moving face in response to feedback from one or more of at least one sensor for measuring the position of the moving face of the actuator relative to a body of the actuator, and the at least one sensor for measuring the gap between the first plate and the second plate.

6. The simulation press as set forth in claim 1, wherein the at least one feedback sensor further comprises at least one sensor for measuring the load of at least one of the first and second plates.

7. The simulation press as set forth in claim 6, wherein the drive controller alters the force generated within the actuator to control the motion of the moving face in response to feedback from the at least one sensor for measuring the load of at least one of the first and second plates.

8. The simulation press as set forth in claim 6, further comprising at least one sensor for measuring the position of the moving face of the actuator relative to a body of the actuator, wherein the drive controller alters the force generated within the actuator to control the motion of the moving face in response to feedback from one or more of at least one sensor for measuring the position of the moving face of the actuator relative to a body of the actuator, and the at least one sensor for measuring the load of at least one of the first and second plates.

9. The simulation press as set forth in claim 1, wherein the at least one feedback sensor further comprises at least one sensor for measuring the inertial force of at least one of the first and second plates.

10. The simulation press as set forth in claim 9, wherein the drive controller alters the force generated within the actuator to control the motion of the moving face in response to feedback from the at least one sensor for measuring the inertial force of at least one of the first and second plates.

11. The simulation press as set forth in claim 9 further comprising at least one sensor for measuring the position of the moving face of the actuator relative to a body of the actuator, wherein the drive controller alters the force generated within the actuator to control the motion of the moving face in response to feedback from one or more of the at least one sensor for measuring the position of the moving face of the actuator relative to a body of the actuator, and the at least one sensor for measuring the inertial force of at least one of the first and second plates.

12. The simulation press as set forth in claim 1, wherein the first plate is coupled to the main body via a coupling structure, the coupling structure comprising at least one temperature modification plate between the first plate and the main body for varying the temperature of the first plate and at least one insulating plate between the at least one temperature modification plate and the main body for insulating the main body from the at least one temperature modification plate.

13. The simulation press as set forth in claim 1, wherein the second plate is coupled to the actuator via a coupling structure, the coupling structure comprising at least one temperature modification plate between the second plate and the actuator for varying the temperature of the second plate and at least one insulating plate between the at least one temperature modification plate and the actuator for insulating the actuator from the at least one temperature modification plate.

14. The simulation press as set forth in claim 1, wherein surfaces of the first plate and the second plate are adapted to simulate at least one of an activation, fusion bonding, embossing, crimping, perforating, stretching, and cutting process.

15. The simulation press as set forth in claim 1, wherein the main body is substantially heavier and more rigid relative to other components of the simulation press.

16. The simulation press as set forth in claim 1, further comprising one or more air bags operably coupled to the main body and supporting the main body.

17. A press for simulating loading of an area on a workpiece comprising:
  a main base, the main base being substantially rigid;
  an actuator attached to the main base, the actuator having a moving face and being substantially axially aligned with a longitudinal axis of symmetry of the main base, and the moving face adapted to move generally linearly in the same plane as the main base;
  a first plate operably coupled to the actuator;
  a second plate operably coupled to the main base with a coupling unit, the coupling unit comprising:
    at least one support plate; and
    at least one sensor comprising at least one of:
    at least one position feedback sensor for determining the distance between the first plate and the second plate;
    at least one load feedback sensor for measuring the load of the second plate; and
    at least one force feedback sensor for measuring the inertial force of the second plate; and
  a drive controller coupled to the actuator for controlling the operation of the actuator in response to feedback from the at least one sensor, so as to cause the first plate to move relative to the second plate such that the first and second plates engage at least one area on a workpiece;
  wherein at least one plate is able to be rotated, angled, or both rotated and angled.

18. The press for simulating loading of an area on a workpiece of claim 17, wherein the first plate is removably coupled to the actuator with a second coupling unit for movement with the moving face of the actuator, the second coupling unit comprising at least one heating and cooling plate coupled to the first plate, the heating and cooling plate being adapted to change temperature.

19. The press for simulating loading of an area on a workpiece of claim 18, further comprising at least one insulation plate between the at least one heating and cooling plate and the moving face of the actuator.

* * * * *